United States Patent
Modak et al.

(10) Patent No.: US 7,745,425 B2
(45) Date of Patent: *Jun. 29, 2010

(54) NON-IRRITATING COMPOSITIONS CONTAINING ZINC SALTS

(75) Inventors: Shanta M. Modak, River Edge, NJ (US); Milind S. Shintre, Pune (IN); Lauserpina Caraos, New York, NY (US); Trupti Gaonkar, New York, NY (US); Ingrid Geraldo, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 859 days.

This patent is subject to a terminal disclaimer.

(21) Appl. No.: 11/327,677

(22) Filed: Jan. 6, 2006

(65) Prior Publication Data

US 2007/0020342 A1 Jan. 25, 2007

Related U.S. Application Data

(63) Continuation-in-part of application No. 11/143,012, filed on Jun. 2, 2005, now Pat. No. 7,563,461, which is a continuation-in-part of application No. 11/031,258, filed on Jan. 7, 2005, now Pat. No. 7,435,429, which is a continuation-in-part of application No. 10/892,034, filed on Jul. 15, 2004, which is a continuation-in-part of application No. 10/622,272, filed on Jul. 17, 2003, which is a continuation-in-part of application No. PCT/US03/03896, filed on Feb. 7, 2003.

(51) Int. Cl.
*A61K 31/60* (2006.01)
*A61K 31/315* (2006.01)
*A61K 33/32* (2006.01)

(52) U.S. Cl. .................. 514/159; 514/494; 424/641; 424/642

(58) Field of Classification Search .................. 514/159, 514/494; 424/641, 642

See application file for complete search history.

(56) References Cited

U.S. PATENT DOCUMENTS

| | | |
|---|---|---|
| 3,257,276 A | 6/1966 | Broh-Kahn et al. |
| 3,485,915 A | 12/1969 | Gerstien et al. |
| 3,960,745 A | 6/1976 | Billany et al. |
| 4,243,657 A | 1/1981 | Okumura et al. |
| 4,318,907 A | 3/1982 | Kligman et al. |
| 4,393,076 A | 7/1983 | Noda et al. |
| 4,478,853 A | 10/1984 | Chaussee et al. |
| 4,587,266 A | 5/1986 | Verdicchio |
| 4,604,384 A | 8/1986 | Smith et al. |
| 4,814,334 A | 3/1989 | Salkin |
| 4,853,978 A | 8/1989 | Stockum |
| 4,868,169 A | 9/1989 | O'Laughlin et al. |
| 4,870,108 A | 9/1989 | Page |
| 4,889,844 A | 12/1989 | Silvetti, Sr. et al. |
| 4,910,205 A | 3/1990 | Kogan et al. |
| 4,919,837 A | 4/1990 | Gluck |
| 4,956,170 A | 9/1990 | Lee et al. |
| 4,963,591 A | 10/1990 | Fourman et al. |
| 4,966,754 A | 10/1990 | Purohit et al. |
| 5,031,245 A | 7/1991 | Milner |
| 5,059,416 A | 10/1991 | Cherukuri et al. |
| 5,073,372 A | 12/1991 | Turner et al. |
| 5,089,205 A | 2/1992 | Huang et al. |
| 5,110,809 A | 5/1992 | Wang et al. |
| 5,116,602 A | 5/1992 | Robinson et al. |
| 5,133,090 A | 7/1992 | Modak et al. |
| 5,147,648 A | 9/1992 | Bannert |
| 5,164,107 A | 11/1992 | Khan et al. |
| 5,208,031 A | 5/1993 | Kelly |
| 5,357,636 A | 10/1994 | Dresdner, Jr. et al. |
| 5,403,864 A | 4/1995 | Bruch et al. |
| 5,447,930 A | 9/1995 | Nayak |
| 5,516,510 A | 5/1996 | Beilfuss et al. |
| 5,591,442 A | 1/1997 | Diehl et al. |
| 5,599,549 A | 2/1997 | Wivell et al. |
| 5,612,324 A | 3/1997 | Guang Lin et al. |
| 5,624,675 A | 4/1997 | Kelly |
| 5,624,962 A | 4/1997 | Takeuchi et al. |
| 5,648,389 A | 7/1997 | Gans et al. |

(Continued)

FOREIGN PATENT DOCUMENTS

DE 4140474 6/1993

(Continued)

OTHER PUBLICATIONS

Modak et al., 2005, A topical cream containing a zinc gel (allergy guard) as a prophylactic against latex glove-related contact dermatitis. Dermatitis. 16(1):22-7.

(Continued)

*Primary Examiner*—Raymond J Henley, III
(74) *Attorney, Agent, or Firm*—Baker Botts L.L.P.

(57) ABSTRACT

The present invention relates to methods and compositions which employ low concentrations of combinations of zinc salts to prevent the irritation of skin or mucous membranes that may be caused by therapeutic agents, by personal hygiene products, by articles such as gloves or condoms, or by various physical, chemical, mechanical, or biological irritants.

67 Claims, No Drawings

U.S. PATENT DOCUMENTS

| | | |
|---|---|---|
| 5,658,575 A | 8/1997 | Ribier et al. |
| 5,705,532 A | 1/1998 | Modak et al. |
| 5,708,023 A | 1/1998 | Modak et al. |
| 5,736,574 A | 4/1998 | Burnier et al. |
| 5,750,122 A | 5/1998 | Evans et al. |
| 5,753,270 A | 5/1998 | Beauchamp et al. |
| 5,763,412 A | 6/1998 | Khan et al. |
| 5,776,430 A | 7/1998 | Osborne et al. |
| 5,804,203 A | 9/1998 | Hahn et al. |
| 5,830,488 A | 11/1998 | Suzuki et al. |
| 5,885,562 A | 3/1999 | Lowry |
| 5,902,572 A | 5/1999 | Luebbe et al. |
| 5,906,808 A | 5/1999 | Osborne et al. |
| 5,951,993 A | 9/1999 | Scholz et al. |
| 5,965,137 A | 10/1999 | Petrus |
| 5,965,310 A | 10/1999 | Yamana |
| 5,965,610 A | 10/1999 | Modak et al. |
| 5,980,477 A | 11/1999 | Kelly |
| 5,980,925 A | 11/1999 | Jampani et al. |
| 5,985,918 A | 11/1999 | Modak et al. |
| 5,985,931 A | 11/1999 | Modak et al. |
| 5,989,531 A | 11/1999 | Schamper et al. |
| 6,022,551 A | 2/2000 | Jampani et al. |
| 6,037,386 A | 3/2000 | Modak et al. |
| 6,040,347 A | 3/2000 | Cupferman et al. |
| 6,045,817 A | 4/2000 | Ananthapadmanabhan et al. |
| 6,107,261 A | 8/2000 | Taylor et al. |
| 6,110,908 A | 8/2000 | Guthery |
| 6,136,771 A | 10/2000 | Taylor et al. |
| 6,183,766 B1 | 2/2001 | Sine et al. |
| 6,187,327 B1 | 2/2001 | Stack |
| 6,204,230 B1 | 3/2001 | Taylor et al. |
| 6,211,243 B1 | 4/2001 | Johnson |
| 6,248,343 B1 | 6/2001 | Jampani et al. |
| 6,287,577 B1 | 9/2001 | Beerse et al. |
| 6,287,583 B1 | 9/2001 | Warren |
| 6,294,186 B1 | 9/2001 | Beerse et al. |
| 6,319,958 B1 | 11/2001 | Johnson et al. |
| 6,321,750 B1 | 11/2001 | Kelly |
| 6,323,171 B1 | 11/2001 | Fonsny et al. |
| 6,344,218 B1 | 2/2002 | Dodd et al. |
| 6,352,701 B1 | 3/2002 | Scholz et al. |
| 6,376,522 B1 | 4/2002 | Holzl et al. |
| 6,387,357 B1 | 5/2002 | Chopra et al. |
| 6,403,067 B1 | 6/2002 | Schamper et al. |
| 6,403,071 B1 | 6/2002 | Scavone et al. |
| 6,414,032 B1 | 7/2002 | Johnson |
| 6,420,431 B1 | 7/2002 | Johnson |
| 6,426,062 B1 | 7/2002 | Chopra et al. |
| 6,511,657 B2 | 1/2003 | Avendano et al. |
| 6,582,711 B1 | 6/2003 | Asmus et al. |
| 6,613,312 B2 | 9/2003 | Rizvi et al. |
| 6,682,749 B1 | 1/2004 | Potechin et al. |
| 6,723,689 B1 | 4/2004 | Hoang et al. |
| 6,846,846 B2 | 1/2005 | Modak et al. |
| 7,435,429 B2 | 10/2008 | Modak et al. |
| 7,563,461 B2 | 7/2009 | Modak et al. |
| 2002/0022660 A1 | 2/2002 | Jampani et al. |
| 2002/0098159 A1 | 7/2002 | Wei et al. |
| 2002/0165130 A1 | 11/2002 | Johnson et al. |
| 2003/0134780 A1 | 7/2003 | Patt |
| 2003/0152644 A1 | 8/2003 | Modak et al. |
| 2003/0157138 A1 | 8/2003 | Eini et al. |
| 2003/0211066 A1 | 11/2003 | Scholz et al. |
| 2004/0102429 A1 | 5/2004 | Modak |
| 2004/0208908 A1 | 10/2004 | Modak et al. |
| 2004/0219227 A1 | 11/2004 | Modak |
| 2004/0247685 A1 | 12/2004 | Modak |
| 2004/0253275 A1 | 12/2004 | Eini et al. |
| 2005/0019431 A1 | 1/2005 | Modak et al. |
| 2005/0048139 A1 | 3/2005 | Modak |
| 2005/0124725 A1 | 6/2005 | Modak |
| 2005/0192547 A1 | 9/2005 | Modak |
| 2005/0238602 A1 | 10/2005 | Modak et al. |
| 2005/0281762 A1 | 12/2005 | Modak et al. |
| 2006/0099237 A1 | 5/2006 | Modak |
| 2006/0141017 A1 | 6/2006 | Kling et al. |
| 2008/0075761 A1 | 3/2008 | Modak |
| 2008/0311231 A1 | 12/2008 | Modak |
| 2009/0004122 A1 | 1/2009 | Modak |
| 2009/0029961 A1 | 1/2009 | Modak |
| 2009/0035228 A1 | 2/2009 | Modak |
| 2009/0035390 A1 | 2/2009 | Modak |
| 2009/0175806 A1 | 7/2009 | Modak |

FOREIGN PATENT DOCUMENTS

| | | |
|---|---|---|
| DE | 4240674 | 3/1994 |
| EP | 304802 | 3/1989 |
| EP | 0313302 | 4/1989 |
| EP | 402078 | 9/1992 |
| EP | 0521455 | 1/1993 |
| EP | 0604484 | 7/1994 |
| EP | 0604848 | 7/1994 |
| EP | 0694310 | 1/1996 |
| FR | 2729050 | 7/1996 |
| JP | 10328284 | 12/1998 |
| RU | 2166309 | 5/2001 |
| SU | 833240 | 5/1981 |
| WO | WO8400111 | 1/1984 |
| WO | WO8704350 | 7/1987 |
| WO | WO8800795 | 2/1988 |
| WO | WO8803799 | 6/1988 |
| WO | WO8905645 | 6/1989 |
| WO | WO9307903 | 4/1993 |
| WO | WO9318745 | 9/1993 |
| WO | WO9318852 | 9/1993 |
| WO | WO9415461 | 7/1994 |
| WO | WO9526134 | 10/1995 |
| WO | WO9824426 | 6/1998 |
| WO | WO9851275 | 11/1998 |
| WO | WO9903463 | 1/1999 |
| WO | WO99/38505 | 5/1999 |
| WO | WO9960852 | 12/1999 |
| WO | WO9963816 | 12/1999 |
| WO | WO0037042 | 6/2000 |
| WO | WO0141573 | 6/2001 |
| WO | WO 03/034994 | 5/2003 |
| WO | WO03034994 | 5/2003 |
| WO | WO 03/066001 | 8/2003 |
| WO | WO 03/066001 A2 | 8/2003 |
| WO | WO03066001 | 8/2003 |
| WO | WO03083028 | 10/2003 |
| WO | WO 2004/014416 | 2/2004 |
| WO | WO04014416 | 2/2004 |
| WO | WO 2006/099359 | 9/2006 |
| WO | WO2006099359 | 9/2006 |
| WO | WO2007069214 | 6/2007 |
| WO | WO 2007/069214 | 9/2007 |

OTHER PUBLICATIONS

Cimiotti et al., 2003, "Adverse reactions associated with an alcohol-based hand antiseptic among nurses in a neonatal intensive care unit." Am. J. Infect. Control 31:43-48.

Bleasel et al., 2002, "Allergic contact dermatitis following exposure to essential oils" Australian Journal of Dermatology 43:211-213.

Vilaplana et al., 2002, "Contact dermatitis from the essential oil of tangerine in fragrances" Contact Dermatitis 46:108.

Larsen et al., 2001 "Fragrance contact dermatitis: a worldwide multicenter investigation (Part II)" Contact Dermatitis 44:344-346.

Nair., 2001, "Final report on the safety assessment of Mentha Piperita (Peppermint) oil, Mentha Piperita (Peppermint) Leaf extract, Mentha Piperita (Peppermint) leaf and Mentha Piperita (Peppermint) water" International Journal of Toxicology 20 (Suppl 3):61-73.

Wohrl., 2001 "The significance of fragrance mix, balsam of Peru, colophony and propolis as screening tools in the detection of fragrance allergy" British Journal of Dermatology 145(2):268-273.

Sugiura., 2000, "Results of patch testing with lavender oils in Japan" Contact Dermatitis 43:157-160.

De Groot et al., 1997, "Adverse reactions to fragrances: a clinical review." Contact Dermatitis 36:57-86.

Modak SM, et al., A Topical Zinc Gluconate Gel Composition for the Prevention of latex/Starch Glove Related Allergic Reactions: Pilot Study in Volunteers. In: Programs and Abstracts of the 37th Interscience Conference on Antimicrobial Agents and Chemotherapy, Toronto: 1997; American Society for Microbiology Washington DC. Abstract J -52.

Goodman and Gilman's The Pharmacological Basis of Therapeutics (Goodman Gilman A, Rall TW, Nies AS, Taylor P, ed. (Pergamon Press; Elmsford, N.Y.: 1990).

Bush et al., 1986, "Pig skin as test substrate for evaluating topical antimicrobial activity" J Clin Microbiol 24:343-348.

Meyer et al., 1978, "The skin of domestic mammals as a model for the human skin, with special reference to the domestic pig." Curr. Problem Dematol 7:39-52.

Lansdown, "Interspecies variations in response to topical application of selected zinc compounds," Food Chem Toxicol. Jan. 1991;29(1):57-64.

Rosenthal, S.L.; Effect of Medicaments on the Motility of the Oral Flora with Special Reference to the Treatment of Vincent's Infection; II. Journal of Dental Research; 1943; vol. 22, pp. 491-494.

U.S. Appl. No. 12/444,089, Modak.

U.S. Appl. No. 10/622,272, filed Apr. 13, 2007 Non-Final Office Action.

U.S. Appl. No. 10/622,272, filed Oct. 15, 2007 Response to Non-Final Office Action.

U.S. Appl. No. 10/622,272, filed Jan. 30, 2008 Non-Final Office Action.

U.S. Appl. No. 10/622,272, filed Apr. 28, 2008 Response to Non-Final Office Action.

U.S. Appl. No. 10/622,272, filed Jul. 4, 2008 Final Office Action.

U.S. Appl. No. 10/622,272, filed Nov. 21, 2008 Response to Final Office Action.

U.S. Appl. No. 10/622,272, filed Jan. 22, 2009 Non-Final Office Action.

U.S. Appl. No. 10/622,272, filed Apr. 22, 2009 Response to Non-Final Office Action.

U.S. Appl. No. 10/622,272, filed Jul. 2, 2009 Final Office Action.

U.S. Appl. No. 10/633,204, filed Apr. 4, 2005 Non-Final Office Action.

U.S. Appl. No. 10/633,204, filed Oct. 7, 2005 Response to Non-Final Office Action.

U.S. Appl. No. 10/633,204, filed Nov. 25, 2005 Response to Non-Final Office Action.

U.S. Appl. No. 10/633,204, filed Mar. 22, 2006 Response to Non-Final Office Action.

U.S. Appl. No. 10/633,204, filed Jun. 7, 2006 Non-Final Office Action.

U.S. Appl. No. 10/633,204, filed Nov. 7, 2006 Response to Non-Final Office Action.

U.S. Appl. No. 10/633,204, filed Jun. 2, 2008 Final Office Action.

U.S. Appl. No. 10/633,204, filed Aug. 28, 2008 Response to Final Office Action.

U.S. Appl. No. 10/633,204, filed Oct. 8, 2008 Non-Final Office Action.

U.S. Appl. No. 10/633,204, filed Jan. 8, 2009 Response to Non-Final Office Action.

U.S. Appl. No. 10/633,204, filed Apr. 17, 2009 Final Office Action.

U.S. Appl. No. 10/785,207, filed Nov. 19, 2007 Non-Final Office Action.

U.S. Appl. No. 10/785,207, filed Feb. 19, 2008 Response to Non-Final Office Action.

U.S. Appl. No. 10/785,207, filed May 14, 2008 Final Office Action.

U.S. Appl. No. 10/785,207, filed Aug. 13, 2008 Response to Final Office Action.

U.S. Appl. No. 10/785,207, filed Sep. 22, 2008 Non-Final Office Action.

U.S. Appl. No. 10/785,207, filed Dec. 18, 2008 Response to Non-Final Office Action.

U.S. Appl. No. 10/785,207, filed Mar. 5, 2009 Final Office Action.

U.S. Appl. No. 10/785,207, filed May 28, 2009 Response to Final Office Action.

U.S. Appl. No. 10/785,207, filed Aug. 11, 2009 Non-Final Office Action.

U.S. Appl. No. 10/786,681, filed May 21, 2007 Non-Final Office Action.

U.S. Appl. No. 10/786,681, filed Sep. 6, 2007 Response to Non-Final Office Action.

U.S. Appl. No. 10/786,681, filed Nov. 21, 2007 Final Office Action.

U.S. Appl. No. 10/786,681, filed Feb. 21, 2008 Response to Final Office Action.

U.S. Appl. No. 10/786,681, filed Jul. 7, 2008 Non-Final Office Action.

U.S. Appl. No. 10/786,681, filed Oct. 2, 2008 Response to Non-Final Office Action.

U.S. Appl. No. 10/786,681, filed Dec. 23, 2008 Final Office Action.

U.S. Appl. No. 10/786,681, filed Mar. 23, 2009 Response to Final Office Action.

U.S. Appl. No. 10/786,681, filed May 27, 2009 Non-Final Office Action.

U.S. Appl. No. 10/891,624, filed Apr. 10, 2007 Non-Final Office Action.

U.S. Appl. No. 10/891,624, filed Oct. 3, 2007 Response to Non-Final Office Action.

U.S. Appl. No. 10/891,624, filed Dec. 18, 2007 Final Office Action.

U.S. Appl. No. 10/891,624, filed Apr. 7, 2008 Response to Final Office Action.

U.S. Appl. No. 10/891,624, filed Jul. 24, 2008 Non-Final Office Action.

U.S. Appl. No. 10/891,624, filed Oct. 22, 2008 Response to Non-Final Office Action.

U.S. Appl. No. 10/891,624, filed Jan. 26, 2009 Final Office Action.

U.S. Appl. No. 10/891,624, filed Apr. 23, 2009 Response to Final Office Action.

U.S. Appl. No. 10/891,624, filed Aug. 6, 2009 Non-Final Office Action.

U.S. Appl. No. 10/892,034, filed Jan. 29, 2008 Non-Final Office Action.

U.S. Appl. No. 10/892,034, filed Jun. 17, 2008 Response to Non-Final Office Action.

U.S. Appl. No. 10/892,034, filed Aug. 27, 2008 Final Office Action.

U.S. Appl. No. 10/892,034, filed Jan. 27, 2009 Response to Final Office Action.

U.S. Appl. No. 10/892,034, filed Apr. 8, 2009 Non-Final Office Action.

U.S. Appl. No. 10/892,034, filed Jul. 2, 2009 Response to Non-Final Office Action.

U.S. Appl. No. 11/250,241, filed Jun. 12, 2009 Non-Final Office Action.

U.S. Appl. No. 10/891,624 filed. Jul. 15, 2004.

U.S. Appl. No. 10/622,272, filed Jul. 17, 2003.

U.S. Appl. No. 08/492,080, filed Jun. 28, 1995.

U.S. Appl. No. 08/760,054, filed Dec. 4, 1996.

U.S. Appl. No. 08/871,071, filed Jun. 9, 1997.

U.S. Appl. No. 09/387,550, filed Aug. 31, 1999.

U.S. Appl. No. 10/785,207, filed Feb. 24, 2004.

U.S. Appl. No. 10/786,681, filed Feb. 25, 2004.

U.S. Appl. No. 11/446,347, filed Jun. 2, 2006.

U.S. Appl. No. 10/892,034, filed Jul. 15, 2004.

U.S. Appl. No. 08/218,666, filed Mar. 28, 1994.

U.S. Appl. No. 10/047,631, filed Oct. 23, 2001.

U.S. Appl. No. 10/891624, filed. Nov. 4, 2009, Response to Non-Final Office Action.

U.S. Appl. No. 10/785,207, filed Nov. 2, 2009, Response to Non-Final Office Action.

U.S. Appl. No. 10/786,681, filed. Aug. 27, 2009, Response to Non-Final Office Action.

U.S. Appl. No. 10/786,681, filed. Nov. 24, 2009, Final Office Action.

U.S. Appl. No. 08/492,080, filed. Sep. 13, 1996, Non-Final Office Action.

U.S. Appl. No. 08/492,080, filed. Jan. 13, 1997, Response to Non-Final Office Action.
U.S. Appl. No. 08/492,080, filed Apr. 19, 1997, Final Office Action.
U.S. Appl. No. 08/492,080, filed. Jul. 9, 1997, Response to Final Office Action.
U.S. Appl. No. 08/492,080, filed. Aug. 5, 1997, Examiner Interview Summary Record.
U.S. Appl. No. 08/492,080, filed Aug. 6, 1997, Notice of Allowance.
U.S. Appl. No. 08/760,054, filed. Mar. 28, 1997, Non-Final Office Action.
U.S. Appl. No. 08/760,054, filed Jul. 28, 1997, Response to Non-Final Office Action.
U.S. Appl. No. 08/760,054, filed Nov. 19, 1997, Final Office Action.
U.S. Appl. No. 08/760,054, filed Apr. 17, 1998, Notice of Appeal Filed.
U.S. Appl. No. 08/760,054, filed Apr. 17, 1998, Amendment/Argument after Notice of Appeal.
U.S. Appl. No. 08/760,054, filed May 15, 1998, Advisory Action.
U.S. Appl. No. 08/760,054, filed Aug. 17, 1998, Express Abandonment.
U.S. Appl. No. 08/760,054, filed Aug. 17, 1998, Continuing Prosecution Application-Continuation (ACPA).
U.S. Appl. No. 08/760,054, filed Nov. 24, 1998, Non-Final Office Action.
U.S. Appl. No. 08/760,054, filed Mar. 17, 1999, Response to Non-Final Office Action.
U.S. Appl. No. 08/760,054, filed Jun. 18, 1999, Examiner's Amendment.
U.S. Appl. No. 08/760,054, filed Jun. 21, 1999, Notice of Allowance.
U.S. Appl. No. 08/871,071, filed May 8, 1998, Non-Final Office Action.
U.S. Appl. No. 08/871,071, filed Nov. 9, 1998, Response to Non-Final Office Action.
U.S. Appl. No. 08/871,071, filed Dec. 9, 1998, Terminal Disclaimer Approved.
U.S. Appl. No. 08/871071, filed Dec. 16, 1998, Non-Final Office Action.
U.S. Appl. No. 08/871,071, filed Mar. 19, 1999, Response to Non-Final Office Action.
U.S. Appl. No. 08/871,071, filed Apr. 16, 1999, Notice of Allowance.
U.S. Appl. No.09/387,550, filed Nov. 9, 1999, Notice of Allowance.
U.S. Appl. No. 09/387,550, filed Nov. 4, 2005, Certificate of Correction.
U.S. Appl. No. 09/378,550, filed Nov. 22, 2005, Certificate of Correction.
U.S. Appl. No. 11/446,347, filed Sep. 1, 2009, Non-Final Office Action.
U.S. Appl. No. 10/892,034, filed Oct. 9, 2009. Final Office Action
U.S. Appl. No. 10/622,272, filed Sep. 29, 2009, Response to final Office Action.
U.S. Appl. No. 10/622,272, filed Dec. 21, 2009, Non-Final Office Action.
U.S. Appl. No. 08/218,666, filed Mar. 3, 1995, Non-Final Office Action.
U.S. Appl. No. 08/218,666, filed Sep. 7, 1995, Response to Non-Final Office Action
U.S. Appl. No. 08/218,666, filed Dec. 18, 1995, Final Office Action.
U.S. Appl. No. 10/047,631, filed Nov. 14, 2003, Non-Final Office Action.
U.S. Appl. No. 10/047,631, filed Apr. 16, 2004, Response to Non-Final Office Action.
U.S. Appl. No. 10/047,631, filed Jul. 12, 2004, Notice of Allowance.
3M Avagard Surgical and Healthcare Personnel Hand Antiseptic with Moisturizers news release, 3M Company, Jun. 11, 2001.
3M Avagard Surgical and Healthcare Personnel Hand Antiseptic with Moisturizers product description, 3M Company, 2001.
A-Z of exhibitors; at Central European Coatings Show, PPC 1. Polymers Paint Colour Journal, No. 4433, vol. 190, p. 42, Oct. 1, 2000.
Beilfuss, "A multifunctional ingredient for deodorants," SOFW Journal, 1998, vol. 124, p. 360, 362-364, 366.
Bezic et al., 2003, "Composition and antimicrobial activity of Achillea clavennae L. essential oil." Phytother. Res. 17(9):1037-1040.

Brehm-Stecher et al. 2003, "Sensitization of *Staphylococcus aureus* and *Escherichia coli* to antibiotics by the sesquiterpenoids nerolidol, farnesol, bisabolol, and apritone." Antimicrobial Agents and Chemotherapy, 47(10):3357-3360.
de Abreu Gonzaga et al., "Composition and antibacterial activity of the essential oils from Zanthoxylum rhoifolium." 2003, Planta Med. 69(8):773-775.
"Drug Information for the Health Care Professional," vol. 1A, USP-D1, 1989, Ninth Edition, pp. 792-793, Banta Company, VIR.
Fitzgerald, K.A., Davies, A., and Russel, A.D., "Mechanism of Action of Chlorhexidine Diacitate and Phenoxyethanol Singly and in Combination Against Gram-negative Bacteria," 215 Mibrobio 70:215-229 (1992).
"Fraicheur de Peau Fresh Skin Body Mist," International Product Alert, No. 9, vol. 14, May 5, 1997.
Garcia et al., 2003,"Virucidal activity of essential oils from aromatic plants of San Luis, Argentina." Phytother. Res. 17(9):1073-1075.
Goren et al., 2003, "Analysis of essential oil of Coridothymus capitatus (L.) and its antibacterial and antifungal activity." Z. Naturforsch. 58(9-10):687-690.
Hajhashemi et al., 2003, "Anti-inflammatory and analgesic properties of the leaf extracts and essential oil of Lavandula angustifolia Mill." Ethnopharmacol. 89(1 ):67-71.
Happi, Household & Personal Products Industry: New ingredients galore at SCC supplier's day, Chemical Business Newsbase, Aug. 1,2000.
Heard, D.D., and Ashworth, R.W., "The Colloidal Properties of Chlorhexidine and its Interaction with Some Macromolecules," J. Pharm. Phannac. 20:505-12, 1968.
Lawless, Julia. The Illustrated Encyclopedia of Essential Oils: The Complete Guide to the Use of Oils in Aromatherapy and Herbalism. Element Books, 1995, USA. pp. 132,162164,169,223,227 and 228.
Lawrence, J.C. et al., "Evaluation of Phenoxeotol—Chlorhexidine Cream as a Prophylactic Antibacterial Agent in Burns," the Lancet, pp. 1037-1040, May 8, 1992.
Manufacturing Chemist: Japan approve Schulke & Mayr's Sensiva SC 50, Chemical Business Newsbase, Jul. 14, 2000.
Minami et al., 2003, "The inhibitory effect of essential oils on herpes simplex virus type-1 replication in vitro." Microbial Immunol. 47(a):681-684.
Modak S. et al., "Rapid Inactivation of Infections Pathogess by Chlorhexidine Coated Gloves," Infection Control and Hospital Epidemiology, 13:463-471, (1992).
Modak Sm, et al., "A Topical Zinc Gluconate Gel Composition for the Prevention of latex/Starch Glove Related Allergic Reactions: Pilot Study in Volunteers." In: Programs and Abstracts of the 37th Interscience Conference on Antimicrobial Agents and Chemotherapy, Toronto: 1997; American Society for Microbiology Washington DC. Abstract J -52.
Molnycke Healthcare, "Hibiclens Antiseptic/Antimicrobial Skin Cleanser" Nov. 10, 2006.
Paranagama et al., 2003, "Fungicidal and anti-aflatoxigenic effects of the essential oil of Cymbopogon citratus (DC.) Stapf. (lemongrass) against Aspergillus flavus Linle isolated from stored rice." Lett. Appi. Microbiol. 37(1):86-90.
Parfums, Cosmetiques, Aromes: Japan approves sale of new cosmetics ingredient, Chemical Business Newsbase, Jan. 16,2001.
Physicians Desk Reference—39th Edition, 1985, p. 1858, Lotrisone.
Physicians Desk Reference—39th Edition, 1985, pp. 2037-2038, chlorhexidine.
Physicians Desk Reference—40th Edition, 1986, pp. 1781-1782, chlorhexidine.
Pfizer "Purell Instant Hand Sanitizer, Product Description" Nov. 10, 2006.
Prevacare: Antimicrobial Hand Gel product description, Johnson & Johnson, Advanced Wound Care, 2001.
Prevcare: Total solution skin care spray product description, Johnson & Johnson, Advanced Wound Care, 2001.
Robinson, K. "Heat beating technology; deodorant market," Soap Perfumery and Cosmetics, v. 69 No. 7 p. 34, Jul. 1996.

Rubbo et al., "A Review of Sterilization and Disinfection," Year Book Medical Publishers, Chicago, 161-162 (1965).

S &M in Japan - Schulke & Mayr's Sensiva SC 50 deodorant active ingredient received approval for use in the Japanese market, SPC Asia No. 21, p. 35, May 2000.

Schmolka, I.R., "The Synergistic Effects of Nonionic Surfactants Upon Cationic Germicidal Agents," J. Soc. Cosmet. Chem., 24:577-592, 1973.

Schuhmacher et al., 2003, "Virucidal effect of peppermint oil on the enveloped viruses herpes simplex virus type 1 and type 2 in vitro." Phytomedicine 10:504-510.

Schwarzkopf: Moving into a new era, European Cosmetic Markets, Sep. 1, 1996.

Schwarzkopf cares, European Cosmetic Markets, No. 5, vol. 13, May 1, 1996.

Sensiva SC 50 product description from manufacturer website (www.schuelkemayr.corn), Schulke & Mayr, manufacturer, printed Apr. 4, 2001.

Shin, 2003, "Anti-Aspergillus activities of plant essential oils and their combination effects with ketoconazole or amphotericin B." Arch. Pharrn. Res. 26(5):389-393.

Silva et al., 2003, "Analgesic and anti-inflammatory effects of essential oils of Eucalyptus." Ethnopharmacoi. 89(2-3);277-283.

SPC, Soap Perfumery and Cosmetics: New for deodorants: Sensiva SC 50, Chemical Business Newsbase, Aug. 12, 1999.

Valero and Salmera, 2003, "Antibacterial activity of 11 essential oils against Bacillus cereus in tyndallized carrot broth." Int. Food Microbiol. 85(1-2): 73-81.

Velluti et al., 2003, "Inhibitory effect of cinnamon, clove, lemongrass, oregano and palmarose essential oils on growth and fumonisin B1 production by Fusarium proliferatum in maize grain." Int. Food Microbiol. 89: 145-154.

Vichy launches oil-free moisturizer, Chemist & Druggist, p. 792, Jun. 8, 1996.

Woodruff,1 . "Mixed feelings," Soap Perfumery & Cosmetics, No. 9, vol. 73, p. 39, Sep. 1, 2000.

NON-IRRITATING COMPOSITIONS CONTAINING ZINC SALTS

CROSS REFERENCE TO RELATED APPLICATIONS

The present invention is a continuation-in-part of U.S. patent application Ser. No. 11/143,012, filed Jun. 2, 2005, which issued as U.S. Pat. No. 7,563,461 on Jul. 21, 2009, which is a continuation-in-part of U.S. patent application Ser. No. 11/031,258, filed Jan. 7, 2005, which issued as U.S. Pat. No. 7,435,429 on Oct. 14, 2008, which is a continuation-in-part of U.S. patent application Ser. No. 10/892,034, filed Jul. 15, 2004, which is a continuation-in-part of U.S. patent application Ser. No. 10/622,272, filed Jul. 17, 2003, which is a continuation-in-part of International Patent Application PCT/US03/03896, filed Feb. 7, 2003, published in English as WO03/066001 on Aug. 14, 2003, which claims priority to Provisional Patent Application No. 60/355,549, filed Feb. 7, 2002, now expired, the contents of each of which are incorporated herein by reference in their entireties.

1. INTRODUCTION

The present invention relates to methods and compositions which employ low concentrations of combinations of zinc salts to prevent the irritation of skin or mucous membranes that may be caused by therapeutic agents, by personal hygiene products, by hygenic or protective articles such as gloves, or by various physical, chemical, mechanical, or biological irritants.

2. BACKGROUND OF THE INVENTION

The Center for Disease Control (CDC) estimates that hospital-acquired infections cost the U.S. healthcare system $4.5 billion a year, and that 80% of these infections are transmitted by direct touch. Although the simple use of soap before and after direct contact with a patient can reduce the transmission of these infections, health care workers often fail to employ this simple measure for several reasons. First, washing with soap and water takes time. Second, such washing necessitates the use of running water, sinks, paper towels and other infrastructural needs that are expensive to provide and maintain and therefore not always immediately accessible by healthcare personnel. Thus, most health care workers follow the existing washing guidelines only about 50% of the time.

In response to this problem, the CDC recently issued new hand hygiene guidelines for health care workers. One recommendation is for doctors, nurses and other health care workers to use alcohol-based hand antiseptics rather than traditional water-based soaps to decontaminate their hands between contact with each patient to prevent the spread of infections. This new CDC guideline is expected to reduce the time spent to decontaminate hands and hence increase compliance among health-care workers. Moreover, the recommended alcohol-based products can be carried with the health care worker or installed in several convenient places near patient rooms. The alcohol in the lotion will kill the bacteria, and added emollients should keep the hands soft. Furthermore, the product dries on the hands, so running water, sinks, paper towels, etc. are largely unnecessary.

A product called Avagard™, made by 3M, is commercially available having a combination of emulsifiers, namely Beheneth-10, behenyl alcohol, cetylpalmitate, and diisopropyl dimer dilinoleate with 1% chlorhexidine gluconate solution and 61% ethyl alcohol (w/w).

A product called Prevacare D™, made by Johnson & Johnson, is commercially available having 60% ethanol as its active ingredient, water as a vehicle, liposome-building blocks including glycerol distearate, stearate-10, cholesterol, and polysorbate 80, sodium laureth sulfate as a surfactant, propylene glycol as a moisturizer, and preservatives including diazolidinyl urea, methylparaben, and propylparaben. Prevacare-D™ is a commercially available product having 60% ethanol as its active ingredient, and also includes cyclomethicone as an emollient, polyethylene and silica as viscosity builders, mineral oil as a moisturizer/emollient, propylparaben as a preservative and fragrance.

A principal drawback with the increased use of alcohol-based products such as Avagard™, Prevacare D™, or others presently available or embodied in various issued U.S. or European patents (see e.g. U.S. Pat. No. 3,485,915, U.S. Pat. No. 4,478,853, U.S. Pat. No. 4,956,170, U.S. Pat. No. 5,403,864, U.S. Pat. No. 5,516,510, U.S. Pat. No. 5,776,430, U.S. Pat. No. 5,885,562, U.S. Pat. No. 5,951,993, U.S. Pat. No. 6,022,551, U.S. Pat. No. 6,107,261, U.S. Pat. No. 6,136,771, U.S. Pat. No. 6,204,230, U.S. Pat. No. 6,352,701, and European Patent Application 0604 848) is that certain ingredients in the formulations, including the alcohol itself, may cause irritation and allergic reactions on the skin. This drawback was readily apparent in a recent study of alcohol-based disinfectants among nurses, which showed that adverse reactions occurred in approximately 12% of all individuals following exposure to these products (Cimiotti et al., 2003, *Am. J. Infect. Control* 31:43-48). The instant invention provides one means of overcoming this problem. Certain zinc salts may be added to alcohol-based gels, hand scrubs or other products to prevent the irritation that may otherwise be caused by the alcohol or other active or inactive ingredients that they may contain (see e.g. U.S. Pat. No. 5,965,610 and U.S. Pat. No. 5,985,918, the contents of which are incorporated by reference herein).

Transmission of infectious diseases is also a serious public health concern outside of the health care setting. For example, a growing number of infectious agents may be transmitted by sexual contact, and public health experts increasingly advocate the use of various devices or substances to reduce or prevent the transmission of infectious agents during sexual contact. Unfortunately, such devices or substances often contain irritating components or ingredients that may cause irritation or the dermis or mucous membranes, thereby actually increasing the risk of infection. For example, male or female condoms are often made from latex or other potentially irritating substances. Genital creams, lotions or ointments often contain potentially irritating microbicides, fungicides or spermicides.

In addition to or as an alternative to antimicrobial topical formulations, gloves are used by health care practioners and in other sectors, such as the food service industry, as a means of preventing spread of infection. However, many persons have or develop sensitivities to gloves, including allergic reactions to latex or dermatologic reactions to moisture retention.

Therefore, the primary means of preventing spread of infection are associated with skin irritation. There is a need to develop products that inhibit or prevent this irritation as a step toward making anti-infective formulations and articles more user-friendly and increasing compliance.

It has been recognized that zinc salts can inhibit irritation caused by a variety of agents. See for example, U.S. Pat. Nos. 5,708,023, 5,965,610, 6,037,386, and 5,985,918, These patents teach the use of relatively high concentrations of zinc, which might be detrimental if taken internally. Apart from the potential for systemic zinc toxicity following the absorption of high concentration water-soluble zinc salts through the skin or mucosa following their use in topical creams or gels, zinc itself may be an irritant at high concentrations. Thus, there is a practical upper limit to the amount of zinc in products designed for internal use. Further, as a result of the ability of zinc to bind to and subsequently inactivate potential irritants such as the contraceptive or antiseptic agent, the inclusion of high concentrations of zinc salts in these products may render them ineffective for their intended functions.

U.S. Pat. Nos. 5,980,477 and 6,321,750 of Kelly relate to the incorporation of water-soluble, organic salts of zinc as anti-viral agents into genital lubricants or other similar products. Kelly does not appreciate or describe the beneficial anti-irritant effects of low concentrations of combinations of water-soluble, organic salts of zinc.

3. SUMMARY OF THE INVENTION

The present invention relates to combinations of two or more water-soluble zinc salts which, when applied to articles or when intermixed with topical formulations can minimize or prevent irritation to the skin or mucus membrane. When added to water- or alcohol-based topical hand scrubs, the anti-irritant properties of the zinc salts described herein may permit the use of higher, otherwise irritating, concentrations of antimicrobial agents, thereby promoting rapid kill of microorganisms and reducing the transmission of infectious diseases in hospital settings. These same zinc salt combinations may be added to gels, creams or lubricants containing spermicides, microbicides, fungicides or other potentially-irritating therapeutic agents, to reduce or prevent irritation of skin or mucosal membranes to which these therapeutic agents are applied. When incorporated into genital lubricants, the reduction in irritation of the vaginal mucosa may assist in minimizing the spread of sexually-transmitted diseases Applied as a coating to articles such as gloves, condoms, or wound dressings, the anti-irritant formulations of the invention may decrease sensitivity to latex or other structural materials and inhibit irritation caused by moisture. In preferred non-limiting embodiments, the present invention provides for formulations and coating for articles comprising two or more water soluble zinc salts each having a molar solubility in water of about 0.17-1.64 moles/liter at 25 degrees Celsius, wherein the total weight percent of all water soluble zinc salts is between about 0.1 and 0.5 percent.

4. DETAILED DESCRIPTION OF THE INVENTION

The present invention relates, at least in part, to methods and compositions for the prevention of irritation of skin or mucosal surfaces that may occur as a result of exposure to irritant substances. It is based, at least in part, on the discovery that the addition of combinations of water-soluble, especially organic, salts of zinc to gels (including hydroalcoholic gels), creams, lotions, ointments, soaps, washes, contraceptive gels, lubricants, elixirs, oils, scrubs, pastes, masks, etc., can increase the ability of these formulations to prevent irritants from causing irritation of the underlying substrate. While it had been found previously that high concentrations of zinc salts added to formulations may enhance the protective effects of these products, zinc itself at high concentrations has been shown to produce irritation. Furthermore, high concentrations of zinc ions in these products also raise the potential for local or systemic zinc toxicity in subjects who use these products. One surprising aspect of the instant invention, therefore, is the finding that low concentrations of zinc salts, especially when two or more such salts are used in combination, can achieve a satisfactory degree of anti-irritant effect while minimizing the potential for both zinc-induced irritation and toxicity. A further advantage of the present approach is that the concentrations of the combination of zinc salts advocated in the present invention are sufficiently low so that their addition to formulations containing biologically-active agents such as spermicides, microbicides, fungicides or other potentially-irritating therapeutic compounds may not be expected to result in the inactivation of these compounds.

In addition, the present invention provides for the use of low concentrations of water soluble zinc salts, optionally in combination with water insoluble zinc salts, in coatings applied to articles that come in contact with the skin. Such articles include, but are not limited to, barrier articles such as gloves, condoms, and diaphrams, as well as articles such as eye protection devices, medical drapes, protective clothing, footware, wound dressings, surgical masks, etc.

Accordingly, in various embodiments, the present invention provides for anti-irritant formulations and coatings comprising low concentrations of two or more water-soluble salts of zinc that are effective in preventing or reducing irritation.

The term "low concentration" means that the weight percent of a zinc salt (including the zinc ion and its binding partner) is less than 2 weight percent, for example between about 0.05 and 2 weight percent, or between about 0.1 and 2 weight percent, or between about 0.1 and 1 weight percent or between about 0.1 and 0.5 weight percent or between about 0.5 and 2 weight percent. Preferably, the water-soluble salts of zinc are present in the compositions (formulations and coatings) of the present invention in a total amount (weight of all water soluble zinc salts combined) of between about 0.1 and 0.5 weight percent, or less than 0.3 percent, or less than or equal to 0.2 percent.

"Water soluble" zinc salts exhibit a molar solubility in water of at least 0.1 moles/liter and preferably at least 0.17 moles/liter, at 25 degrees Celsius. Water soluble zinc salts for use in these formulations include zinc acetate (molar solubility in water of 1.64 moles/l at 25 degrees Celsius), zinc butyrate (molar solubility in water of 0.4 moles/l), zinc gluconate (molar solubility in water of 0.28 moles/l), zinc glycerate (moderately water soluble), zinc glycolate (moderately water soluble), zinc formate (molar solubility in water of 0.33 moles/l at 20 degrees Celsius), zinc lactate (molar solubility in water of 0.17 moles/l), zinc picolinate (moderately water soluble), zinc propionate (molar solubility in water of 1.51 moles/l), zinc salicylate (low water solubility), zinc tartrate (moderately water soluble) and zinc undecylenate (moderately water soluble). In preferred non-limiting embodiments, the present invention provides for formulations and coating for articles comprising two or more water soluble zinc salts each having a molar solubility in water of about 0.17-1.64 moles/liter, wherein the total weight percent of all water soluble zinc salts is between about 0.1 and 0.5 percent or less than or equal to about 0.3 percent.

A "water insoluble" zinc salt, as that term is used herein, refers to a compound having a water solubility of less than 0.1 moles/liter at 25 degrees Celsius. Non-limiting examples of water insoluble zinc salts include zinc oxide, zinc stearate, zinc citrate, zinc phosphate, zinc carbonate, and zinc borate. In specific, non-limiting embodiments, the water insoluble zinc salt is present in a concentration of between about 0.05 and 2 weight percent or between about 0.1 and 1 percent.

In further specific, non-limiting embodiments, the total amount of all zinc salts, including water soluble and water insoluble salts, is between about 0.1 and 5 weight percent, or between about 0.1 and 2 weight percent, or between about 0.1 and 1 weight percent.

The terms "prevention" or "reduction" of irritation means a decrease in objective or subjective signs of irritation in tissues treated with the formulations comprising low concentrations of two or more water-soluble, organic salts of zinc of at least 50%, and more preferably by greater than 90% relative to control tissues exposed to the irritant agent and the same formulations lacking zinc salts. Irritation in this context may be evidenced by redness or other changes in coloration, inflammation or swelling, hypersensitivity, the occurrence of burning, itching or other painful stimuli, chapping, wrinkling, rash, hives or other macroscopic or microscopic changes known to those of ordinary skill in the art to be associated with irritation.

The formulations of the invention may be applied topically to the skin or to the various mucous membranes of the body, including but not limited to those of the oral, nasal, vaginal or rectal cavities, to prevent the effects of exogenous irritants upon these surfaces. The formulations of the invention may be used as disinfectants, for example handscrubs to be used prior to donning surgical gloves.

The formulations of the invention may be applied as coatings to articles, for example barrier articles, and as such may, in an article having more than one surface, coat at least one surface (the entire surface or a portion thereof) of the article. As specific, non-limiting embodiments, a coating according to the invention may be applied to the inner surface of a glove or condom, or to the outer surface of a glove or condom, or to both inner and outer surfaces of a glove or condom. Different coatings may be applied to each surface. A coating may be applied over a portion of a surface, for example, but not by way of limitation, on the inner surface of one or more fingertip of a glove.

Various embodiments of the invention may comprise an emollient, such as, but not limited to, PEG 20 almond glycerides, Probutyl DB-10, Glucam P-20, Glucam E-10, Glucam P-10, Glucam E-20, Glucam P-20 distearate, Procetyl-10 (Croda), Incroquat, glycerin, propylene glycol, cetyl acetate, and acetylated lanolin alcohol, cetyl ether, myristyril ether, hydroxylated milk glycerides, polyquaternium compounds, copolymers of dimethyl dialyl ammonium chloride and acrylic acid, dipropylene glycol methyl ethers, polypropylene glycol ethers and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_2$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Further emollients include lanolin, olive oil, cocoa butter, and shea butter. The present invention provides for the incorporation, into formulations and coatings, of one or more emollient solvent. Preferred emollient solvents of the invention include octoxylycerin (Sensiva®), pentylene glycol, 1,2 hexanediol and caprylyl glycol, for example, and not by way of limitation, at a concentration of up to 5 percent or up to 3 percent.

Various embodiments of the invention may comprise a stabilizing agent, such as, but not limited to, an antioxidant (which may be at a concentration of 0.2-1%), such as but not limited to vitamin C (ascorbic acid) or vitamin E (tocopherol).

The stabilizing agents surprisingly appear to remove the turbidity of the formulations, resulting in a clear product that imparts a light feel to the surface to which it is applied.

Various embodiments of the invention may comprise a thickening agent, such as but not limited to the following (at a preferred concentration of 0.6-2%): stearyl alcohol, cationic hydroxy ethyl cellulose (U Care JR30; Amerchol), hydroxy propyl methyl cellulose, hydroxy propyl cellulose (Klucel), Polyox N-60K, chitosan pyrrolidone carboxylate (Kytamer), behenyl alcohol, zinc stearate, Crodamol STS (Croda) or an emulsifying wax, such as but not limited to, Incroquat and Polawax. Other thickening and/or gelling agents suitable for incorporation into the formulations or ointments described herein include, for example, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, crodomol, crothix, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminum silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminum silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/glycerin/glycidyl decanoate copolymer, ophthalmic/trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof.

An embodiment of the invention may comprise phenoxyethanol (0.3-1.0%) as a solubilizing agent.

Various embodiments of the invention may comprise a humectant, such as but not limited to glycerin, panthenol, Glucam P20, 1-2-propylene glycol, dipropylene glycol, polyethylene glycol, 1,3-butylene glycol, or 1,2,6-hexanetriol.

Various embodiments of the invention may comprise one or more antimicrobial or preservative agent, preferably at a total concentration between 0.05 and 5 weight percent or between 0.05 and 2 weight percent or between 0.1 and 2 weight percent. Examples of preferred antimicrobial and/or preservative agents include, but are not limited to, chlorhexidine gluconate (CHG), benzalkonium chloride (BZK), or iodopropynylbutyl carbamate (IPBC; Germall plus). Further examples of antimicrobial agents include, but are not limited to, iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzethonium chloride (BZT), dequalinium chloride, biguanides such as chlorhexidine (including free base and salts (see below)), PHMB (polyhexamethylene biguanide), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, and pharmaceutically acceptable salts thereof.

Pharmaceutically acceptable chlorhexidine salts that may be used as antimicrobial agents according to the invention include, but are not limited to, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. Chlorhexidine free base is a further example of an antimicrobial agent.

These and further examples of antimicrobial agents useful in this invention can be found in such references as Goodman and Gilman's The Pharmacological Basis of Therapeutics (Goodman Gilman A, Rall T W, Nies A S, Taylor P, ed. (Pergamon Press; Elmsford, N.Y.: 1990)), the contents of which are hereby incorporated by reference.

Various embodiments of the invention may comprise a neutralizing agent to neutralize carboxyl groups present in one or more other component, such as carboxyl groups in a thickening agent. Suitable neutralizing agents include diisopropylamine and triethanolamine.

Various embodiments of the invention may comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. Preferred surfactants include lauroyl ethylenediamine triacetic acid sodium salt at a concentration between about 0.5-2.0%, Pluronic F87 at about 2.0%, Masil SF-19 (BASF) ans incromide. Suitable concentrations of surfactant are between about 0.05% and 2%.

Water used in the formulations described herein is preferably deionized water having a neutral pH. When used in hydroalcoholic gel compositions, the concentration of water should be suitable to dissolve the hydrogels according to the invention. Alcohols that may be used according to the invention include but are not limited to ethanol and isopropyl alcohol.

Various embodiments of the invention may comprise additional additives, including but not limited to a silicone fluid (such as dimethicone or cyclomethicone), a silicone emulsion, dyes, fragrances, pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as Germall plus and DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate O, phenylbenzimidazole, sulfonic acid, sulisobenzone, titanium dioxide, trolamine salicylate and zinc oxide.

Various embodiments of the invention may comprise an essential oil ("EO"), which is a volatile oil obtained from a plant or an animal source that comprises one or more active agent (also referred to herein as an Isolated Component or "IC") which may be, for example but not by way of limitation, a monoterpene or sesquiterpene hydrocarbon, alcohol, ester, ether, aldehyde, ketone, or oxide. Examples of these EOs include, but are not limited to, almond oil, ylang-ylang oil, neroli oil, sandalwood oil, frankincense oil, peppermint oil, lavender oil, jasmine absolute, geranium oil bourbon, spearmint oil, clove oil, lemongrass oil, cedarwood oil, balsam oils, and tangerine oil. Alternatively, the present invention provides for the use of active agents found in essential oils (ICs) such as, but not limited to, 1-citronellol, α-amylcinnamaldehyde, lyral, geraniol, farnesol, hydroxycitronellal, isoeugenol, eugenol, eucalypus oil and eucalyptol, lemon oil, linalool, and citral. Apart from their effects as fragrances or flavorants, such compounds also may be useful in the instant invention as antimicrobial agents. The concentrations of EO or IC may be between about 0.3 and 1 percent or between about 0.1 and 0.5 percent or between 0.5 and 2 percent (all weight percent values).

A hydrogel, as used herein, may comprise hydroxypropylmethyl cellulose, cationic hydroxyethyl cellulose (U-care polymers), ethyl cellulose, hydroxypropyl cellulose, hydroxymethyl cellulose, hydroxypropyl methyl cellulose (methocell K4MS) carboxy methyl cellulose, polyethylene oxide (polyox resins), or chitosan pyrrolidone carboxylate (Kytomer PC). These hydrogels preferably do not adversely bind to any added antimicrobial agent, therefore leaving the optionally added antimicrobial agent free for rapid and long-term activity. In addition, it has been discovered that alcohol used to form the hydroalcoholic gel is not trapped in the hydroalcoholic gel composition and is therefore available for rapid and long-term action. The hydrogel may be present in a concentration between 0.1-1.0%, and preferably is a cationic hydroxyethyl cellulose (U-care polymers) in a concentration between 0.05-0.5%, most preferably 0.2%.

In hydroalcoholic gel compositions of the invention, alcohols that may be used include aliphatic alcohols, including, but not limited to, ethanol, isopropyl alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol. The concentration of alcohol may be between 30% and 95%, preferably between 40% and 70%; preferably the aliphatic alcohols is ethanol or isopropyl alcohol at a concentration between and 60% and 95%. When present, the concentration of fatty alcohols is preferably between 0.5% and 5.0%; and, when present, the concentration of hexanol is preferably between 3% and 10%, more preferably 5%. These same emulsifiers may be used in other formulations of the invention as well.

Hydroalcoholic gel compositions of the invention may optionally comprise an emollient and/or humectant such as the emollients and humectants discussed above, preferably one or more of PEG 20 Almond Glycerides, Probutyl DB-10, Glucam P20, Glucam E-10, Glucam P-10, Glucam E-20, Glucam P-20 distearate, glycerin, propylene glycol, octoxyglycerin (Sensiva®), cetyl acetate and acetylated lanolin alcohol (Acetulan), cetyl ether (PPG-10), myristyl ether (PPG-3), hydroxylated milk glycerides (Cremerol HMG), polyquaternium compounds (U-care compounds), chitosan (Kytamer), copolymer of dimethyl dialyl ammonium chloride and acrylic acid (Merquat), dipropylene glycol methyl ethers (Dowanol DPM Dow Corning), or polypropylene glycol ethers (Ucon 50-HB-660, Union Carbide). Preferably the emollient is present at a concentration of 3% or less, such that the viscosity of the composition is preferably less than 2000 centipoise at 20-40° C., more preferably between 0.2 and 3%.

Hydroalcoholic gel compositions of the invention may optionally comprise a surfactant and/or emulsifier, such as the emulsifiers and surfactants discussed above, and preferably a non-ionic or cationic self-emulsifying wax that is soluble in alcohol at ambient temperature. Suitable surfactant/emulsifiers include but are not limited to Incroquat Behenyl TMS, Incroquat Behenyl TMS-50, Polawax, stearyl alcohol and cetearyl alcohol. These emulsifiers may be present at a concentration between 0.05-3.0%. Preferred emulsifiers include Incroquat Behenyl TMS, which is a mild cationic emulsifier as well as an excellent conditioner, and Polawax, which is a non-ionic self emulsifying wax, individually at a concentration of between 0.05-0.5%, and in combination at a concentration of between 0.05-0.5%, more preferably in combination at a concentration ratio of approximately 1:1. If more than one emulsifier is used, it is preferred that the total concentration of emulsifiers present is between 0.05-0.5%.

A hydroalcoholic gel of the invention may optionally comprise a silicone polymer such as, but not limited to, one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), or silicone glycol (BASF 1066 DCG polyol). Preferred concentrations of silicone polymer are between about 0.1-1.0%.

A hydroalcoholic gel of the invention may optionally comprise an emollient solvent such as, but are not limited to, those listed above or one or more than one glycidyl ethers having alkyl chains up to and including 18 carbon molecules and ethoxylates and propoxylates thereof, glyceryl ethers having alkyl chains up to and including 18 carbon molecules and ethoxylates and propoxylates thereof, mono- and diglyceryl ethers having alkyl chains up to and including 18 carbon molecules and ethoxylates and propoxylates thereof, ethoxylate and propoxylate ethers, ethoxy diglycol esters, ethyl hexyl alcohol propoxylate, propylene glycol esther ethoxylates or propoxylates, or, preferably Arlamol (Altas). Preferred concentrations of emollient solvent are between 0.5-5%.

A hydroalcoholic gel of the invention may optionally comprise a thickening agent, such as, but not limited to, a thickening and/or gelling agent discussed above, preferably behenyl alcohol, crodomol, or crothix. Preferred concentrations of thickening agent are between 0.05-10%. Gelling agents such as Caropol are not preferred due to their high viscosity and their requiring neutralizing agents to neutralize the gelling agent with alkaline materials.

A hydroalcoholic gel of the invention may optionally comprise one or more antimicrobial agent, such as those set forth above. Preferably, the concentration of the one or more than one antimicrobial agent is less than 3%. In particular non-limiting embodiments of the invention, hydroalcoholic gels may comprise chlorhexidine gluconate, benzalkonium chloride and phenoxyethanol, preferably at a concentration of between 0.05-0.5%, 0.1-0.25%, and 0.1-1.0%, respectively. Because cationic antimicrobials, such as biguanides and quaternary ammonium compounds, can bind to the surface of the skin, they may not be available to inactivate pathogens that come into contact with the skin. The gel formulation according to the invention preferably forms a film on the surface of the hand when applied, which film acts as a barrier preventing the antimicrobial agents that may be added to the gel from binding to the surface of the skin.

Ambient temperature is defined herein between 20 and 35° C. Room temperature is defined herein between 20 and 25° C.

The present invention further provides for spermicidal gels, creams, lubricants, lotions or ointments containing low concentrations of two or more water-soluble, organic salts of zinc that are effective in reducing or preventing the irritation caused by the spermicidal agent. Such formulations may be applied topically to the skin or mucosa of the urogenital, perineal area, or to the surface of latex articles such as male or female condoms, to prevent the irritating effects of spermicides that are incorporated into the gel. These products have the additional advantage of minimizing or preventing irritation caused by allergic reaction to latex. Spermicidal agents are well known to those of ordinary skill in the art, and include, but are not limited to, detergent-based spermicides.

In non-limiting embodiments, a composition of the invention may comprise a pre-existing formulation, such as a commercially available cream, liquid, gel or lotion. Examples of commercially available formulations that may be so used include, but are not limited to, personal lubricants sold under the trade names "KY JELLY," "ASTROGLIDE," and "PRE-VACARE" and lotions sold under the trade names "SOFT-SENSE," "LOTION SOFT," "CUREL," and "KERI". SOFT-SENSE (Johnson & Son, Inc., Racine, Wis.) is known to contain purified water, glycerin USP, distearyldimonium chloride, petrolatum USP, isopropyl palmitate, 1-hexadecanol, tocopheryl acetate (vitamin E USP), dimethicone, titanium dioxide USP, methyl paraben, propyl paraben, sodium chloride, and fragrance. LOTION SOFT (Calgon Vestal, St. Louis, Mo.) is a nonionic moisturizing lotion which is known to contain mucopolysaccharide. CUREL (Bausch & Lomb Incorporated, Rochester, N.Y.) is known to contain deionized water, glycerin, quaternium-5, petrolatum, isopropyl palmitate, 1-hexadecanol, dimethicone, sodium chloride, fragrance, methyl paraben, and propyl paraben.

The invention provides for methods of using the foregoing compositions to prevent irritation to an epithelial tissue (e.g. a mucosal tissue or the skin) comprising applying an effective amount of the composition to the surface or coating an article which is intended to come into contact with the skin or a mucosal tissue. Examples of irritants against which protection may be afforded include, but are not limited to, those induced by physical, chemical, mechanical or biological irritants. Specific examples of the foregoing irritants include, but are not limited to, means for hair removal (e.g. depilatories, waxing and razors), hair relaxants (e.g. sodium hydroxide, calcium hydroxide, thioglycolates), antiperspirants (e.g. aluminum chlorhydrate and other aluminium salts), dermatological treatments (e.g. alpha hydroxy acids (AHAs), especially glycolic and trichloroacetic acids), keratoyltic skin-irritating conditions (e.g. psoriasis, dandruff, etc.), infectious skin irritants (e.g. bacteria and fungi), and agents applied for therapeutic purposes. The epithelial surface to be protected from irritation may be dermal or mucosal, including vaginal, anorectal, oral or nasal.

The invention further provides for methods of protecting against infection comprising applying, to an epithelial tissue such as the skin or a mucous membrane of the body, an effective amount of one of the foregoing compositions which inhibits irritation of the tissue. Examples of infectious agents against which protection may be afforded include, but are not limited to, infectious agents associated with sexually transmitted diseases, including Human Immunodeficiency Virus (HIV), Human Papilloma Virus (HPV), Herpes Simplex Virus (HSV), *Chlamydia trachomatis, Neisseria gonorrhoea, Trichomonas vaginalis,* and *Candida albicans,* as well as infectious agents that may be encountered in a health care setting, including but not limited to *Staphylococcus aureus, Pseudomonas aeruginosa, Streptococcus pneumoniae, Escherichia coli, Salmonella typhimurium, Enterococcus,* and *Neisseria meningitidis,* HIV, varicella virus and Hepatitis viruses (e.g., A, B, and C).

In non-limiting embodiments, the present invention provides for a topical composition comprising an antimicrobial composition that comprises an emollient solvent and an essential oil (or active component (IC) thereof). Although such topical compositions may optionally contain additional antimicrobial (including preservative) compounds, in preferred non-limiting embodiments, the antimicrobial composition consists essentially of an emollient solvent and an essential oil (see the following paragraph). Said composition may additionally comprise an anti-inflammatory agent, for example, but not limited to, salicylic acid, acetyl salicylic acid, or zinc salicylate. The topical composition may, or alternatively may not, comprise one or more zinc salt, which may be a water-soluble organic zinc salt such as those listed herein. The present invention further provides for methods for producing an antimicrobial effect on the skin or mucous membrane of a subject using such topical compositions.

In certain alternative non-limiting embodiments, the formulations and/or coatings of the invention lack an antimicrobial agent selected from the group consisting of iodophors, iodine, benzoic acid, dihydroacetic acid, propionic acid, sorbic acid, methyl paraben, ethyl paraben, propyl paraben, butyl paraben, cetrimide, quaternary ammonium compounds, including but not limited to benzalkonium chloride, dequalinium chloride, biguanides such as chlorhexidine (including free base and salts (see below)), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, and pharmaceutically acceptable salts thereof.

In still further embodiments, the present invention provides for a zinc slurry that may be applied to a latex article (such as a condom or glove) to reduce or prevent irritation. The zinc slurry may comprise, for example but not by way of limitation, at least two water-soluble zinc salts (as set forth above) at a concentration of between 1-5%, one or more water-insoluble zinc salts (as set forth above) at a concentration of 2-10%, panthenol at a concentration of 5-40%, and glycerine at a concentration of 20-50%. Such a slurry may be mixed with a liquid, such as a silicone fluid, in a ratio of between 1:5 to 1:10, and then applied to the surface of the article which will be in contact with the skin. In a specific embodiment nonlimiting embodiment, the present invention provides for an emulsion which may be used to coat the interior surface of a glove, such as a latex glove, and prevent or reduce irritation as follows: zinc acetate (0.40% by weight), zinc g/uconate (0.30% by weight), U Care JR-30M (0.05% by weight), D,L-Panthenol 50W (1.00% by weight), zinc lactate (1.60% by weight), zinc oxide (0.20% by weight), glycerin (3.00% by weight), purified water (10.00% by weight) and silicone emulsion (83.45% by weight). In particular non-limiting embodiments, the total amount of all water-soluble zinc salts present in such a slurry is between 0.1 and 0.5 weight percent.

In one particular set of non-limiting embodiments, the present invention provides for a coating for application to or as applied on an article, comprising two water soluble zinc salts, each at a concentration of between 0.1 and 1 weight percent, a first water insoluble zinc salt at a concentration of between about 0.1 and 1 weight percent, a derivative of pantothenic acid, such as panthenol, at a concentration of between about 0.5 and 5 weight percent or between about 0.5 and 5 weight percent, and optionally glycerin, at a concentration of between 2 and 5 weight percent. Coating solutions may further comprise a silicone emulsion at a concentration between about 70 and 95 weight percent. In certain non-limiting embodiments, said coating further comprises a third water soluble zinc salt at a concentration of between 0.1 and 1 weight percent. In certain non-limiting embodiments, in such coatings, which optionally comprise a third water soluble zinc salt, the combined amounts of all water soluble zinc salts is between about 0.5 and 0.5 weight percent, or the combined amounts of all zinc salts (water soluble and water insoluble) may be between about 0.1 and 5 weight percent, or between about 0.1 and 2 weight percent, or between about 0.1 and 1 weight percent. In still other non-limiting embodiments, such coatings may further comprise a second water insoluble zinc salt.

In another particular set of non-limiting embodiments, the present invention provides for a coating for application to an article, comprising two water soluble zinc salts, each at a concentration of between 0.1 and 1 weight percent, a first water insoluble zinc salt at a concentration of between about 0.1 and 1 weight percent, a derivative of pantothenic acid, such as panthenol, at a concentration of between about 0.05 and 5 weight percent, or between about 0.5 and 5 weight percent, an effective amount of one or more antimicrobial agent, and optionally glycerin, at a concentration of between 2 and 5 weight percent. Coating solutions may further comprise a silicone emulsion at a concentration between about 70 and 95 weight percent. Suitable antimicrobial agents include, but are not limited to, biguanides, iodophors, quaternary ammonium compounds, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylenol, foscarnet, miconazole, fluconzaole, itriconazole and ketoconazole. In non-limiting embodiments, the amount of antimicrobial agent may be as set forth above for particular agents, and/or may be between about 0.05 and 5 weight percent, or between about 0.05 and 2 weight percent, or between about 0.05 and 1 weight percent. In certain non-limiting embodiments, said coating further comprises a third water soluble zinc salt at a concentration of between 0.1 and 1 weight percent. In certain non-limiting embodiments, in such coatings, which optionally comprise a third water soluble zinc salt, the combined amounts of all water soluble zinc salts is between about 0.1 and 0.5 weight percent or the combined amounts of all zinc salts (water soluble and water insoluble) may be between about 0.1 and 5 weight percent, or between about 0.1 and 2 weight percent, or between about 0.1 and 1 weight percent. In still other non-limiting embodiments, such coatings may further comprise a second water insoluble zinc salt.

The present invention further provides for coatings as set forth above, further comprising an emollient solvent, preferably at a concentration of less than 5 or less than 3 weight percent.

In yet another set of non-limiting embodiments, the present invention provides for articles, such as but not limited to barrier articles, having at least one surface to which one of the foregoing coatings has been applied. The coating may cover said entire surface or a portion of it. In specific non-limiting embodiments of the invention, the article may be a glove, a condom, a diaphragm, a drape, a piece of surgical apparel, a surgical mask, or a wound dressing.

Percentages herein are weight/weight unless specified otherwise.

The present invention further provides for topical compositions comprising two or more salts of zinc, each having a molar solubility in water of between about 0.17-1.64 moles/liter, wherein said salts of zinc in total are present at a combined concentration of between about 0.1% and 0.5% weight/weight, and further comprising water, ethanol, and one or more agent selected from the group consisting of a thickening agent, an antimicrobial agent, a surfactant, an emulsifier, and an emollient.

In specific non-limiting embodiments, said topical composition may be a surgical hand wash or "hand prep", comprising (i) two or more organic salts of zinc, each having a molar solubility in water of between about 0.17 and 1.64 moles/liter, wherein said organic salts of zinc in total are present at a combined concentration of between about 0.1 and 0.5 percent (weight/weight); (ii) farnesol at a concentration of between about 0.3 and 1.0 percent (weight/weight); (iii) panthenol at a concentration of between about 0.2 and 5 percent (weight/weight); and (iv) a quaternary ammonium compound and a biguanide, wherein the total concentration of quaternary ammonium compound and biguainde is between about 0.05 and 2.0 percent (weight/weight). In preferred, nonlimiting embodiments the organic salts of zinc are zinc gluconate, present at a concentration of between about 0.10-0.25 percent (weight/weight) and zinc lactate, present at a concentration of about between about 0.10-0.25 percent (weight/weight).

In further embodiments of the invention, said topical composition may be a disinfectant soap, comprising: (i) two or more organic salts of zinc, each having a molar solubility in water of between about 0.17 and 1.64 moles/liter, wherein said organic salts of zinc in total are present at a combined concentration of between about 0.1 and 0.5 percent (weight/weight); (ii) farnesol at a concentration of between about 0.3 and 1.0 percent (weight/weight); (iii) panthenol at a concentration of between about 0.2 and 5 percent (weight/weight); and (iv) a quaternary ammonium compound and a second antimicrobial agent selected from the group consisting of a biguanide and a chlorinated phenol, wherein the total concentration of quaternary ammonium compound and second antimicrobial agent is between about 0.05 and 2.0 percent (weight/weight). In preferred non-limiting embodiments, the organic salts of zinc are zinc gluconate, present at a concentration of between about 0.10-0.25 percent (weight/weight) and zinc lactate, present at a concentration of about between about 0.10-0.25 percent (weight/weight). In specific non-limiting embodiments, the foregoing disinfectant soaps may further comprise phenoxyethanol at a concentration of between about 0.3 and 1 percent (weight/weight).

Preparation of the soap formulation may be prepared as described. A Phase A solution is prepared by preparing a 5% Zinc solution (50% Zinc Gluconate and 50% Zinc lactate) and adding in 2 grams of the 5% zinc solution is added to 69.92 DI water. A Phase B solution is prepared by adding to the Phase A solution, the following ingredients:

0.2% Polyox N60K, 2.0% Pluronic F 87 Prill, 0.4% U-care, 0.15 Germall Plus

The solution is mixed after the addition of each ingredient. The solution is then mixed for approximately 45 minutes or until all ingredients are properly dissolved.

To the above solution (phase A+phase B) add: the Phase C solution as follows:

1.0% D-L Panthenol 3.0% Montaline 3.0% Incromine oxide L 1.0% PxE 2.0% Glycerin 2.0% B65C The solution is mixed well after the addition of each ingredient.

Phase D solution is prepared as follows:

In 14.0% SD alcohol 40B dissolve:

0.18% BZT 0.75% PHMB 0.3% Farnesol

Phase D is added to the mixture of previous phases A-C and mixed well. A desired color and/or fragrance is also added.

Specific non-limiting working examples are set forth below.

5. WORKING EXAMPLES

Healthcare Handwash I

| Constituent | % (w/w) |
|---|---|
| Silicone Fluid 245 (Dow Corning) | 0.50 |
| Panthenol 50W (BASF) | 1.00 |
| Zinc lactate | 0.20 |
| Benzethonium chloride | 0.18 |
| Procetyl-10 (Croda) | 0.50 |
| Zinc gluconate | 0.20 |
| Vitamin E acetate | 0.10 |
| U Care JR 30M (Amerchol) | 0.05 |
| Farnesol | 0.30 |
| Glucam P20 (Chemron) | 0.50 |
| Incroquat TMS Behenyl (Croda) | 0.80 |
| Methocell K4MS (Dow) | 0.10 |
| Polawax A31 | 0.80 |
| Incroquat B65C (Croda) | 0.30 |
| Glucam E-10 (Chemron) | 0.50 |
| Cosmocil CQ [PHMB (20% solution)] | 0.75 |
| Alcohol (SDA-40B) | 51.67 |
| Water | 41.55 |
| Fragrance | 50 µl |

Surgical Hand Prep (General formula)

| Constituent | % (w/w) |
|---|---|
| Essential Oil/and or constituents | 0.3-1.0 |
| Alkylpropoxylate | 0-2.0 |
| Polyquaternium 10 | 0.05-0.5 |
| Derivative of Pantothenic Acid | 0.5-2.0 |
| Alkyl Glycol | 0-2.0 |
| Soluble Zinc Salt #1 | 0.05-0.3 |
| Alkylarylpropoxylate | 0-2.0 |
| Soluble Zinc Salt #2 | 0-0.3 |
| Quaternary Ammonium Compounds | 0-0.2 |
| Hydroxyalkylcellulose | 0-0.3 |
| Quaternary conditioners | 0-2.0 |
| Biguanide | 0.05-2.0 |
| Alcohol | 65-73.00 |
| Water | 18-30 |

Biguanide: Chlorhexidine or PHMB

Surgical Hand Prep 213+

| Constituent | % (w/w) |
|---|---|
| Farnesol | 0.50 |
| Procetyl-10 (Croda) | 0.50 |
| U Care JR 30M (Amerchol) | 0.20 |
| Panthenol 50W (BASF) | 1.00 |
| Propylene glycol | 1.00 |
| Zinc gluconate | 0.20 |
| Crodamol STS (Croda) | 1.00 |
| Zinc lactate | 0.20 |
| Benzethonium chloride | 0.18 |
| Methocell K4MS (Dow) | 0.10 |
| Incroquat B65C (Croda) | 0.30 |
| Cosmocil CQ [PHMB (20% solution)] | 0.75 |
| Alcohol (SDA-40B) | 73.00 |
| Water | 21.07 |

Surgical Hand Prep 213+ A

| Constituent | % (w/w) |
|---|---|
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Incroquat B65C (Croda) | 0.30 |
| Cosmocil CQ [PHMB (20% solution)] | 0.75 |
| Alcohol (SDA-40B) | 73.00 |
| Water | 20.67 |

Surgical Hand Prep 213B

| Constituent | % (w/w) |
|---|---|
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Glucam P-20 | 0.5 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Incroquat B65C (Croda) | 0.30 |
| Cosmocil CQ [PHMB (20% solution)] | 1.25 |
| Alcohol (SDA-40B) | 73.00 |
| Water | 19.67 |

Surgical Hand Prep 213B*

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Glucam P-20 | 0.5 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Cosmocil CQ [PHMB (20% solution)] | 1.25 |
| Alcohol (SDA-40B) | 73.00 |
| Water | 19.97 |

Surgical Hand Prep 213G-3

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Incroquat B65C (Croda) | 0.30 |
| Cosmocil CQ [PHMB (20% solution)] | 1.25 |
| Alcohol (SDA-40B) | 73.00 |
| Water | 20.17 |

Surgical Hand Prep 250

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Cosmocil CQ [PHMB (20% solution)] | 0.75 |
| Alcohol (SDA-40B) | 73.00 |
| Water | 20.97 |

Surgical Hand Prep 250A

| Constituent | % (w/w) |
| --- | --- |
| Farnesol | 0.50 |
| Glucam P20 | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Cosmocil CQ [PHMB (20% solution)] | 0.75 |
| Alcohol (SDA-40B) | 73.00 |
| Water | 20.97 |

Surgical Hand Prep 250B

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Incroquat B65 (Croda) | 0.30 |
| Cosmocil CQ [PHMB (20% solution)] | 0.75 |
| Alcohol (SDA-40B) | 73.00 |
| Water | 20.67 |

Surgical Hand Prep 250C

| Constituent | % (w/w) |
| --- | --- |
| Farnesol | 0.50 |
| Glucam P20 | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Incroquat B65 (Croda) | 0.30 |
| Cosmocil CQ [PHMB (20% solution)] | 0.75 |
| Alcohol (SDA-40B) | 73.00 |
| Water | 20.67 |

Surgical Hand Prep 250P

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Glucam P20 | 0.5 |
| Cosmocil CQ [PHMB (20% solution)] | 0.75 |

-continued

Surgical Hand Prep 250P

| Constituent | % (w/w) |
| --- | --- |
| Alcohol (SDA-40B) | 73.00 |
| Water | 20.47 |

Surgical Hand Prep 250BP

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzethonium chloride | 0.18 |
| Methocell K4MS (Dow) | 0.10 |
| Incroquat B65 (Croda) | 0.30 |
| Cosmocil CQ [PHMB (20% solution)] | 0.75 |
| Alcohol (SDA-40B) | 73.00 |
| Glucam P 20 | 0.5 |
| Water | 20.17 |

Surgical Hand Prep 251

| Constituent | % (w/w) |
| --- | --- |
| Farnesol | 0.50 |
| Octoxyglycerine | 2.0 |
| Procetyl-10 (Croda) | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzalkoniumchloride | 0.12 |
| Methocell K4MS (Dow) | 0.10 |
| Cosmocil CQ [PHMB (20% solution)] | 0.75 |
| Alcohol (SDA-40B) | 73.00 |
| Water | 19.03 |

Surgical Hand Prep 251A

| Constituent | % (w/w) |
| --- | --- |
| Farnesol | 0.50 |
| Octoxyglycerine | 2.0 |
| Glucam P20 | 0.50 |
| U Care JR 30M (Amerchol) | 0.20 |
| Panthenol 50W (BASF) | 1.50 |
| Propylene glycol | 1.00 |
| Zinc gluconate | 0.10 |
| Crodamol STS (Croda) | 1.00 |
| Zinc lactate | 0.20 |
| Benzalkoniumchloride | 0.12 |
| Methocell K4MS (Dow) | 0.10 |
| Cosmocil CQ [PHMB (20% solution)] | 0.75 |
| Alcohol (SDA-40B) | 73.00 |
| Water | 20.0 . . . 0 |

Surgical Hand Prep 252

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.0 |
| Propylene glycol | 1.00 |
| Zinc gluconate | 0.10 |
| Crodamol STS (Croda) | 1.00 |
| Zinc lactate | 0.20 |
| Benzalkonium chloride | 0.12 |
| Methocell K4MS (Dow) | 0.10 |
| Cosmocil CQ [PHMB (20% solution)] | 0.75 |
| Alcohol (SDA-3C) | 76.4. |
| Water | 18.13 |

Surgical Hand Prep 252A

| Constituent | % (w/w) |
| --- | --- |
| Farnesol | 0.50 |
| Glucam P20 | 0.50 |
| U Care JR 30M (Amerchol) | 0.20 |
| Panthenol 50W (BASF) | 1.0 |
| Propylene glycol | 1.00 |
| Zinc gluconate | 0.10 |
| Crodamol STS (Croda) | 1.00 |
| Zinc lactate | 0.20 |
| Benzalkonium chloride | 0.12 |
| Methocell K4MS (Dow) | 0.10 |
| Cosmocil CQ [PHMB (20% solution)] | 0.75 |
| Alcohol (SDA-3C) | 76.4. |
| Water | 18.03. |

Surgical Hand Prep 253

| Constituent | % (w/w) |
| --- | --- |
| Farnesol | 0.50 |
| Procetyl-10 (Croda) | 0.50 |
| U Care JR 30M (Amerchol) | 0.20 |
| Panthenol 50W (BASF) | 1.0 |
| Propylene glycol | 1.00 |
| Zinc gluconate | 0.10 |
| Crodamol STS (Croda) | 1.00 |
| Zinc lactate | 0.20 |
| Benzalkonium chloride | 0.12 |
| Methocell K4MS (Dow) | 0.10 |
| Chorhexidine gluconate (20% solution)] | 0.25 |
| Alcohol (SDA-3C) | 76.4. |
| Water | 18.63 |

Surgical Hand Prep 253A

| Constituent | % (w/w) |
| --- | --- |
| Farnesol | 0.50 |
| Glucam P20 | 0.50 |
| U Care JR 30M (Amerchol) | 0.20 |
| Panthenol 50W (BASF) | 1.0 |
| Propylene glycol | 1.00 |
| Zinc gluconate | 0.10 |
| Crodamol STS (Croda) | 1.00 |
| Zinc lactate | 0.20 |

Surgical Hand Prep 253A

| Constituent | % (w/w) |
| --- | --- |
| Benzalkonium chloride | 0.12 |
| Methocell K4MS (Dow) | 0.10 |
| Chorhexidine gluconate (20% solution)] | 0.25 |
| Alcohol (SDA-3C) | 76.4. |
| Water | 18.5 |

Surgical Hand Prep 254

| Constituent | % (w/w) |
| --- | --- |
| Farnesol | 0.50 |
| Octoxyglycerine | 2.0 |
| Procetyl-10 (Croda) | 0.50 |
| U Care JR 30M (Amerchol) | 0.20 |
| Panthenol 50W (BASF) | 1.0 |
| Zinc gluconate | 0.10 |
| Crodamol STS (Croda) | 0.5 |
| Zinc lactate | 0.20 |
| Benzalkonium chloride | 0.12 |
| Methocell K4MS (Dow) | 0.10 |
| Chorhexidine gluconate (20% solution)] | 0.25 |
| Alcohol (SDA-3C) | 76.4. |
| Water | 18.13 |

Surgical Hand Prep 254A

| Constituent | % (w/w) |
| --- | --- |
| Farnesol | 0.50 |
| Octoxyglycerine | 2.0 |
| Glucam P20 | 0.50 |
| U Care JR 30M (Amerchol) | 0.20 |
| Panthenol 50W (BASF) | 1.0 |
| Zinc gluconate | 0.10 |
| Crodamol STS (Croda) | 0.5 |
| Zinc lactate | 0.20 |
| Benzalkonium chloride | 0.12 |
| Methocell K4MS (Dow) | 0.10 |
| Chorhexidine gluconate (20% solution)] | 0.25 |
| Alcohol (SDA-3C) | 76.4. |
| Water | 18.1. |

Surgical Hand Prep 255

| Constituent | % (w/w) |
| --- | --- |
| Farnesol | 0.50 |
| Propylene glycol | 1.0 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Crodamol STS (Croda) | 0.5 |
| Zinc lactate | 0.20 |
| Benzathonium chloride | 0.18 |
| Methocell K4MS (Dow) | 0.05 |
| Incroquat B 65 | 0.3 |
| Chorhexidine gluconate (20% solution)] | 0.25 |
| Alcohol (SDA-3C) | 76.4. |
| Water | 18.32 |

Surgical Hand Prep 255A

| Constituent | % (w/w) |
| --- | --- |
| Farnesol | 0.50 |
| Propylene glycol | 1.0 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Crodamol STS (Croda) | 0.5 |
| Zinc lactate | 0.20 |
| Benzathonium chloride | 0.18 |
| Methocell K4MS (Dow) | 0.05 |
| Incroquat B 65 | 0.3 |
| Chorhexidine gluconate (20% solution)] | 0.25 |
| Alcohol (SDA 40 B) | 73.0. |
| Water | 21.22 |
| Glucam P 20 | 0.5 |

Surgical Hand Prep 256

| Constituent | % (w/w) |
| --- | --- |
| Farnesol | 0.50 |
| Propylene glycol | 1.0 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Crodamol STS (Croda) | 0.5 |
| Zinc lactate | 0.20 |
| Benzathonium chloride | 0.18 |
| Incroquat B 65 | 0.3 |
| Chorhexidine gluconate (20% solution)] | 0.25 |
| Alcohol (SDA 40B) | 73.0. |
| Water | 21.77 |

Surgical Hand Prep 256A

| Constituent | % (w/w) |
| --- | --- |
| Farnesol | 0.50 |
| Propylene glycol | 1.0 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Crodamol STS (Croda) | 0.5 |
| Zinc lactate | 0.20 |
| Benzathonium chloride | 0.18 |
| Glucam P 20 | 0.5 |
| Incroquat B 65 A | 0.3 |
| Chorhexidine gluconate (20% solution)] | 0.25 |
| Alcohol (SDA 40B) | 73.0. |
| Water | 21.27 |

| Surgical Hand Prep 256C | |
|---|---|
| Constituent | % (w/w) |
| Farnesol | 0.50 |
| Propylene glycol | 1.0 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Crodamol STS (Croda) | 0.5 |
| Zinc lactate | 0.20 |
| Benzathonium chloride | 0.18 |
| Glucam P 20 | 0.5 |
| Incroquat B 65 A | 0.3 |
| Chorhexidine gluconate (20% solution)] | 0.25 |
| Alcohol (SDA 3C) | 76.4.0 |
| Water | 17.87 |

| Surgical Hand Prep 256G-1 | |
|---|---|
| Constituent | % (w/w) |
| Farnesol | 0.50 |
| Propylene glycol | 1.0 |
| Glucam P 20 | 0.50 |
| U Care JR 30M (Amerchol) | 0.20 |
| Panthenol 50W (BASF) | 1.5 |
| Zinc gluconate | 0.10 |
| Zinc lactate | 0.20 |
| Benzathonium chloride | 0.18 |
| Incoquat B 65 C | 0.5 |
| PHMB(20% solution)] | 0.75 |
| Alcohol (SDA 40 B) | 73.0 |
| Water | 21.57 |

| Surgical Hand Prep 256G-2 | |
|---|---|
| Constituent | % (w/w) |
| Farnesol | 0.50 |
| Propylene glycol | 1.0 |
| Glucam P 20 | 0.50 |
| U Care JR 30M (Amerchol) | 0.20 |
| Panthenol 50W (BASF) | 1.5 |
| Crodamol STS | 0.5 |
| Zinc gluconate | 0.10 |
| Zinc lactate | 0.20 |
| Benzathonium chloride | 0.18 |
| Incroquat B 65 C | 0.5 |
| PHMB(20% solution)] | 0.75 |
| Alcohol (SDA 40 B) | 73.0 |
| Water | 20.57 |

| Surgical Hand Prep 256G-3 | |
|---|---|
| Constituent | % (w/w) |
| Farnesol | 0.50 |
| Propylene glycol | 1.0 |
| Glucam P 20 | 0.50 |
| U Care JR 30M (Amerchol) | 0.20 |
| Panthenol 50W (BASF) | 1.5 |
| Methocell K4MS (Dow) | 0.1 |
| Zinc gluconate | 0.10 |
| Zinc lactate | 0.20 |

-continued

| Surgical Hand Prep 256G-3 | |
|---|---|
| Constituent | % (w/w) |
| Benzathonium chloride | 0.18 |
| Incoquart B 65 C | 0.5 |
| PHMB(20% solution)] | 0.75 |
| Alcohol (SDA 40 B) | 73.0 |
| Water | 20.97 |

| Surgical Hand Prep 257 | |
|---|---|
| Constituent | % (w/w) |
| Farnesol | 0.50 |
| Octoxyglycerine | 1.0 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Crodamol STS (Croda) | 0.5 |
| Zinc lactate | 0.20 |
| Benzathonium chloride | 0.18 |
| Incroquat B 65 A | 0.3 |
| Chorhexidine gluconate (20% solution)] | 0.25 |
| Alcohol (SDA-40B) | 73. |
| Water | 21.77 |

| Healthcare Handwash (General Formula) | |
|---|---|
| Constituent | % (w/w) |
| Silicone Oil | 0.25-2.0 |
| Derivative of Pantothenic Acid | 0.5-2.0 |
| Soluble Zinc Salt #1 | 0.05-0.3 |
| Quaternary Ammonium Compounds | 0.05-0.2 |
| Alkylpropoxylate | 0.2-2.0 |
| Soluble Zinc Salt #2 | 0.05-0.3 |
| Vitamin E | 0.05-1.0. |
| Polyquaternium 10 | 0.05-0.5 |
| Essential Oil/and or constituents | 0.3-1.0 |
| Alkyl Glucoside # | 0.25-1.0 |
| Fatty Quaternary Amine Salt | 0.1-1.0 |
| Fatty Alcohol | 0.3-3.0 |
| Hydroxyalkylcellulose | 0.05-0.2 |
| Emulsifying Wax | 0.03-1.0 |
| Quaternary Amine Salt | 0.3-2.0 |
| Alkyl Glucoside #2 | 0-1.0 |
| Biguanide | 0.05-2.0 |
| Alcohol | 50-60 |

Biguanide: Chlorhexidine or PHMB

| Zinc Healthcare Handwash (220) | |
|---|---|
| Constituent | % (w/w) |
| Water | 23.67 |
| Zinc lactate | 0.2 |
| Zinc gluconate | 0.2 |
| Methocell K4MS | 0.1 |
| U Care-JR 30M | 0.2 |
| Panthenol 50W | 1.0 |
| BZT | 0.18 |
| Alcohol SDA-3C | 70.4 |
| Crodamol STS | 1.0 |
| Procetyl 10 | 0.5 |

Zinc Healthcare Handwash (220)

| Constituent | % (w/w) |
| --- | --- |
| Incoquart B-65A | 0.3 |
| Propylene glycol | 1.0 |
| Farnesol | 0.5 |
| Cosmocil CQ [PHMB (20% solution)] | 0.75 |

Zinc Healthcare Handwash (220D)

| Constituent | % (w/w) |
| --- | --- |
| Water | 22.97 |
| Zinc lactate | 0.2 |
| Zinc gluconate | 0.2 |
| Methocell K4MS | 0.1 |
| U Care-JR 30M | 0.2 |
| Panthenol 50W | 1.0 |
| BZT | 0.18 |
| Alcohol SDA-3C | 70.4 |
| Crodamol STS | 1.0 |
| Procetyl 10 | 0.5 |
| Glucam P-20 | 0.5 |
| Propylene glycol | 1.0 |
| Farnesol | 0.5 |
| Cosmocil CQ [PHMB (20% solution)] | 1.25 |

Healthcare Handwash (237R)

| Constituent | % (w/w) |
| --- | --- |
| Panthenol 50W (BASF) | 1.00 |
| Zinc lactate | 0.20 |
| Benzethonium chloride | 0.18 |
| Procetyl-10 (Croda) | 0.50 |
| Zinc gluconate | 0.20 |
| U Care JR 30M (Amerchol) | 0.05 |
| Farnesol | 0.50 |
| Glucam P20 (Chemron) | 0.50 |
| Incroquat TMS Behenyl (Croda) | 0.70 |
| Methocell K4MS (Dow) | 0.10 |
| Polawax A31 (Croda) | 0.70 |
| Cosmocil CQ [PHMB (20% solution)] | 1.25 |
| Phenoxyethanol | 0.70 |
| Alcohol (SDA-3C) | 57.0 |
| Water | 36.42 |

Healthcare Haudwash 237R*

| Constituent | % (w/w) |
| --- | --- |
| Silicone Fluid 245 (Dow Corning) | 0.50 |
| Panthenol 50W (BASF) | 1.00 |
| Zinc lactate | 0.20 |
| Benzethonium chloride | 0.18 |
| Procetyl-10 (Croda) | 0.50 |
| Zinc gluconate | 0.20 |
| Vitamin E acetate | 0.10 |
| U Care JR 30M (Amerchol) | 0.05 |
| Farnesol | 0.30 |
| Glucam P20 (Chemron) | 0.50 |
| Incroquat TMS Behenyl (Croda) | 0.80 |
| Methocell K4MS (Dow) | 0.10 |
| Polawax A31 | 0.80 |
| Incroquat B65C (Croda) | 0.30 |

Healthcare Haudwash 237R*

| Constituent | % (w/w) |
| --- | --- |
| Glucam E-10 (Chemron) | 0.50 |
| Cosmocil CQ [PHMB (20% solution)] | 1.25 |
| Alcohol (SDA-40B) | 51.67 |
| Water | 41.05 |
| Fragrance | 50 μl |

Surgical Hand Disinfectant N.A (General Formula)

| Constituent | % (w/w) |
| --- | --- |
| Essential oil ingredient | 0.5-2.0 |
| Alkylpropoxylate | 0-2.0 |
| Polyquaternium-10 | 0.2-0.3 |
| Derivative of Pantothenic Acid | 1.0-5.0 |
| Propylene glycol | 1.0-3.0 |
| Zinc gluconate | 0.1-.2.0 |
| Alkyl Glycol | 0-1.0 |
| Zinc lactate | 0.1-0.2 |
| Emollient solvent | 1.0-5.0 |
| Essential oil | 0.0-0.8 |
| Diazolidinyl urea + Iodopropynyl butylcarbamate | 0.0-0.3 |
| Methocell K4MS ((Hydroxypropylmethyl cellulose) | 0.1-0.2 |
| Phenoxyethanol | 0.5-1.0 |
| Alcohol | 62-75 |
| Water | 20-40 |

Surgical Hand Disinfectant N.A-1

| Constituent | % (w/w) |
| --- | --- |
| Farnesol | 1.00 |
| Procetyl-10 (Croda) | 0.50 |
| U Care JR 30M (Amerchol) | 0.20 |
| Panthenol 50W (BASF) | 1.00 |
| Propylene glycol | 1.00 |
| Zinc gluconate | 0.10 |
| Glucam P.20 | 0.50 |
| Zinc lactate | 0.10 |
| 1,2-octanediol | 3.00 |
| Germal Plus | 0.20 |
| Methocell K4MS (Dow) | 0.10 |
| Phenoxyethanol | 1.00 |
| Alcohol (SDA-3C) | 70.00 |
| Water | 21.3. |

Surgical Hand Disinfectant N.A-2

| Constituent | % (w/w) |
| --- | --- |
| Farnesol | 1.0 |
| Procetyl-10 (Croda) | 0.50 |
| U Care JR 30M (Amerchol) | 0.20 |
| Panthenol 50W (BASF) | 1.00 |
| Propylene glycol | 1.00 |
| Zinc gluconate | 0.10 |
| Glucam P.20 | 0.5 |
| Zinc lactate | 0.10 |
| 1,2-octanediol | 3.0 |
| Chamomile oil | 0.1 |
| Methocell K4MS (Dow) | 0.10 |

-continued

Surgical Hand Disinfectant N.A-2

| Constituent | % (w/w) |
|---|---|
| Phenoxyethanol | 0.5 |
| Alcohol (SDA-3C) | 70.0 |
| Water | 21.9. |

Surgical Hand Disinfectant N.A-3

| Constituent | % (w/w) |
|---|---|
| Farnesol | 0.5 |
| Procetyl-10 (Croda) | 0.50 |
| U Care JR 30M (Amerchol) | 0.20 |
| Panthenol 50W (BASF) | 1.00 |
| Propylene glycol | 1.00 |
| Zinc gluconate | 0.10 |
| Glucam P20 | 0.5 |
| Zinc lactate | 0.10 |
| 1,2-octanediol | 3.0 |
| Methocell K4MS (Dow) | 0.10 |
| Phenoxyethanol | 0.5 |
| Alcohol (SDA-3C) | 77.0 |
| Water | 15.5.0 |

Surgical Hand Disinfectant N.A-4

| Constituent | % (w/w) |
|---|---|
| Farnesol | 0.5 |
| Procetyl-10 (Croda) | 0.50 |
| U Care JR 30M (Amerchol) | 0.20 |
| Panthenol 50W (BASF) | 1.00 |
| Propylene glycol | 1.00 |
| Zinc gluconate | 0.10 |
| Glucam P20 | 0.5 |
| Zinc lactate | 0.10 |
| 1,2-octanediol | 1.0 |
| Octoxy glycerine | 2.0 |
| Incoquart B-65 A | 0.3 |
| Methocell K4MS (Dow) | 0.10 |
| Phenoxyethanol | 0.5 |
| Alcohol (SDA-3C) | 77.0 |
| Water | 15.2.0 |

Surgical Hand Disinfectant N.A-5

| Constituent | % (w/w) |
|---|---|
| Farnesol | 0.5 |
| Procetyl-10 (Croda) | 0.50 |
| U Care JR 30M (Amerchol) | 0.20 |
| Panthenol 50W (BASF) | 1.00 |
| Propylene glycol | 1.00 |
| Zinc gluconate | 0.10 |
| Glucam P20 | 0.5 |
| Zinc lactate | 0.10 |
| Octoxy glycerine | 3.0 |
| Incoquart B-65 A | 0.3 |
| Methocell K4MS (Dow) | 0.10 |
| Phenoxyethanol | 0.5 |
| Alcohol (SDA-3C) | 77.0 |
| Water | 15.2 |

Surgical Hand Disinfectant N.A-6A

| Constituent | % (w/w) |
|---|---|
| Farnesol | 0.5 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Glucam P20 | 0.5 |
| Zinc lactate | 0.10 |
| 1,2-octanediol | 1.0 |
| Octoxy glycerine | 2.0 |
| Incoquart B-65 A | 0.3 |
| Phenoxyethanol | 0.5 |
| Alcohol (SDA-40 B) | 73.0 |
| Water | 19.8. |

Surgical Hand Disinfectant N.A-6C

| Constituent | % (w/w) |
|---|---|
| Farnesol | 0.5 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Glucam P20 | 0.5 |
| Zinc lactate | 0.10 |
| 1,2-octanediol | 1.0 |
| Octoxy glycerine | 2.0 |
| Incoquart B-65 A | 0.3 |
| Phenoxyethanol | 0.5 |
| Alcohol (SDA-40 B) | 76.4. |
| Water | 16.4 |

Surgical Hand disinfectant N.A-6G-1

| Constituent | % (w/w) |
|---|---|
| Farnesol | 0.5 |
| Glucam P 20 | 0.5 |
| U Care JR 30M (Amerchol) | 0.20 |
| Panthenol 50W (BASF) | 1.5 |
| Zinc gluconate | 0.10 |
| Zinc lactate | 0.10 |
| 1,2-octanediol | 1.0 |
| Octoxy glycerine | 2.0 |
| Incoquat B-65 C | 0.5 |
| Phenoxyethanol | 0.5 |
| Alcohol (SDA-40B) | 73.0 |
| Water | 20.1 |

Surgical Hand disinfectant N.A-6G-2

| Constituent | % (w/w) |
|---|---|
| Farnesol | 0.5 |
| Glucam P 20 | 0.5 |
| U Care JR 30M (Amerchol) | 0.20 |
| Panthenol 50W (BASF) | 1.5 |
| Zinc gluconate | 0.10 |
| Zinc lactate | 0.10 |
| 1,2-octanediol | 0.5 |
| Octoxy glycerine | 2.0 |
| Incoquat B-65 C | 0.5 |

Surgical Hand disinfectant N.A-6G-2

| Constituent | % (w/w) |
| --- | --- |
| Phenoxyethanol | 0.5 |
| Alcohol (SDA-40B) | 73.0 |
| Water | 20.6 |

Surgical Hand disinfectant N.A-6G-3

| Constituent | % (w/w) |
| --- | --- |
| Farnesol | 0.5 |
| Glucam P 20 | 0.5 |
| U Care JR 30M (Amerchol) | 0.20 |
| Panthenol 50W (BASF) | 1.5 |
| Crodamol STS | 0.5 |
| Zinc gluconate | 0.10 |
| Zinc lactate | 0.10 |
| 1,2-octanediol | 1.0 |
| Octoxy glycerine | 2.0 |
| Incorquat B-65 C | 0.5 |
| Phenoxyethanol | 0.5 |
| Alcohol (SDA-40B) | 73.0 |
| Water | 19.6 |

Surgical Hand Disinfectant N.A-7

| Constituent | % (w/w) |
| --- | --- |
| Farnesol | 0.5 |
| Procetyl-10 (Croda) | 0.50 |
| U Care JR 30M (Amerchol) | 0.20 |
| Panthenol 50W (BASF) | 1.5 |
| Zinc gluconate | 0.10 |
| Glucam P20 | 0.5 |
| Zinc lactate | 0.10 |
| Octoxy glycerine | 3.0 |
| Incoquart B-65 A | 0.3 |
| Phenoxyethanol | 0.5 |
| Alcohol (SDA-3C) | 76.4 |
| Water | 16.4 |

Surgical Hand Disinfectant N.A-8

| Constituent | % (w/w) |
| --- | --- |
| Farnesol | 0.5 |
| Procetyl-10 (Croda) | 0.50 |
| U Care JR 30M (Amerchol) | 0.20 |
| Panthenol 50W (BASF) | 1.00 |
| Sensiva | 2.0 |
| Zinc gluconate | 0.10 |
| Crodamol STS | 1.0 |
| Zinc lactate | 0.1 |
| Glucam P20 | 0.5 |
| Octanediol | 1.0 |
| Incoquart B-65 A | 0.3 |
| Methocell K4MS (Dow) | 0.05 |
| Phenoxyethanol | 0.5 |
| Alcohol (SDA-40B) | 73.0 |
| Water | 19.25 |

Disinfectant Soap (General formula)

| Constituent | % (w/w) |
| --- | --- |
| Water | 60-75 |
| Derivatives of Pantothenic acid | 0.5-2.0 |
| Alcohol | 0-15 |
| Pluronic gel | 1-2 |
| Quaternized coconut oil | 1-5 |
| Incromine Oxide | 1-3 |
| Soluble zinc salt 1 | 0.05-0.2 |
| Soluble Zinc salt 2 | 0.-0.2 |
| Polyethylene Oxide | 0.05-0.3 |
| Quaternary conditioner | 0-2.0 |
| Polyquaternium 10 | 0.1-0.4 |
| Glycerine | 1-5 |
| Quaternary ammonium compound | 0-0.2 |
| Germall+ | 0-0.2 |
| Phenoxy ethanol | 0.5-1.0 |
| Biguanide | 0-1.0 |
| Essentialoil/and or derivatives | 0.05-1.0 |
| Chlorinated phenol | 0-0.3 |
| Emollient solvent | 0-3.0 |

Disinfectant Soap I

| Constituent | % (w/w) |
| --- | --- |
| Water | 66.75 |
| D-L Panthenol 50W | 1.0 |
| Alcohol (SDA 40B) | 16.0 |
| Pluronic F87 Prill | 2.0 |
| Montaline C-40 (Seppic) | 3.0 |
| Incromine oxide L | 4.0 |
| Zinc Lactate | 0.05 |
| Zinc Gluconate | 0.05 |
| Polyox N-60K | 0.2 |
| Incroquat B65C | 2.0 |
| U-care JR 30M | 0.5 |
| Glycerine | 2.0 |
| BZT | 0.1 |
| TC | 0.3 |
| PxE | 1.0 |
| Cosmocil (PHMB (20%)) | 0.75 |
| Farnesol | 0.3 |

Disinfectant Soap II

| Constituent | % (w/w) |
| --- | --- |
| Water | 69.92 |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 3.0 |
| Zinc Lactate | 0.05 |
| Zinc Gluconate | 0.05 |
| Polyox N-60K | 0.2 |
| Incroquat B65C | 2.0 |
| U-care JR 30M | 0.4 |
| Glycerine | 2.0 |
| BZT | 0.18 |
| Germall+ | 0.15 |
| PxE | 1.0 |
| Cosmocil (PHMB (20%)) | 0.75 |
| Farnesol | 0.3 |

| Disinfectant Soap (29)* | |
|---|---|
| Constituent | % (w/w) |
| Water | 69.42 |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 3.0 |
| Zinc Lactate | 0.05 |
| Zinc Gluconate | 0.05 |
| Polyox N-60K | 0.2 |
| B65C | 2.0 |
| U-care JR 30M | 0.4 |
| Glycerine | 2.0 |
| BZT | 0.18 |
| Germall+ | 0.15 |
| PxE | 1.0 |
| Cosmocil (PHMB (20%)) | 1.25 |
| Farnesol | 0.3 |

| Disinfectant Soap (29A) | |
|---|---|
| Constituent | % (w/w) |
| Water | 71.22. |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 3.0 |
| Zinc Gluconate | 0.1 |
| Polyox N-60K | 0.2 |
| U-care JR 30M | 0.4 |
| Glycerine | 2.0 |
| BZT | 0.18 |
| Germall+ | 0.15 |
| Phenoxy ethanol | 1.0 |
| Cosmocil (PHMB (20%)) | 1.25 |
| Farnesol | 0.5 |

| Disinfectant Soap (29-TC) | |
|---|---|
| Constituent | % (w/w) |
| Water | 71.62. |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 3.0 |
| Zinc Gluconate | 0.1 |
| Polyox N-60K | 0.2 |
| U-care JR 30M | 0.4 |
| Glycerine | 2.0 |
| BZT | 0.18 |
| Germall+ | 0.15 |
| Phenoxy ethanol | 1.0 |
| Cosmocil (PHMB (20%)) | 0.75 |
| Farnesol | 0.3 |
| Triclosan | 0.3 |

| Disinfectant Soap NA-14 | |
|---|---|
| Constituent | % (w/w) |
| Water | 70.6 |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 4.0 |
| Zinc lactate | 0.05 |
| Zinc Gluconate | 0.05 |
| Polyox N-60K | 0.2 |
| U-care JR 30M | 0.5 |
| Glycerine | 2.0 |
| Incoquart B-65 A | 0.3 |
| Octanediol | 1.0 |
| Phenoxy ethanol | 1.0 |
| Farnesol | 0.3 |

| Disinfectant Soap NA-14A | |
|---|---|
| Constituent | % (w/w) |
| Water | 69.6.. |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 4.0 |
| Zinc lactate | 0.05 |
| Zinc Gluconate | 0.05 |
| Polyox N-60K | 0.2 |
| U-care JR 30M | 0.5 |
| Glycerine | 2.0 |
| Incoquart B-65 A | 0.3 |
| Octanediol | 2.0 |
| Phenoxy ethanol | 1.0 |
| Farnesol | 0.3 |

| Disinfectant Soap NA-20 | |
|---|---|
| Constituent | % (w/w) |
| Water | 69.6 |
| D-L Panthenol 50W | 1.0 |
| Alcohol (SDA 40B) | 14.0 |
| Pluronic F87 Prill | 2.0 |
| Montaline C-40 (Seppic) | 3.0 |
| Incromine oxide L | 4.0 |
| Zinc lactate | 0.05 |
| Zinc Gluconate | 0.05 |
| Polyox N-60K | 0.2 |
| U-care JR 30M | 0.5 |
| Glycerine | 2.0 |
| Incoquart B-65 A | 0.3 |
| Octanediol | 2.0 |
| Phenoxy ethanol | 1.0 |
| Farnesol | 0.3 |
| Lavender oil | 0.025 |

| Health Care Hand Disinfectant Formulation with emollient solvents and essential oil/and/or ingredients (General Formula 1) | |
| --- | --- |
| Constituent | % (w/w) |
| Silicone Oil | 0.5-2.0 |
| Derivative of Pantothenic Acid | 0.5-2.0 |
| Soluble Zinc Salt #1 | 0.05-0.2 |
| Alkyarylpropoxylate | 0-1.0 |
| Soluble Zinc Salt #2 | 0.05-0.3 |
| Essential Oil/and or constituents | 0.3-1.0 |
| Fatty Alcohol | 0-1.0 |
| Alcohol | 50-80 |
| Water | 15-30 |
| Carbomer | 0.3-0.5 |
| Neutralizing agent | 1-4.0 |
| Glycerin | 0.5-2.0 |
| Propylene Glycol | 0.5-2.0 |
| Emollient Solvent | 0.5-5.0 |
| Phenoxyethanol | 0.3-1.0 |

| Health Care Hand Disinfectant Formulation with emollient solvents and essential oil/and/or ingredients (specific formula) | |
| --- | --- |
| Constituent | % (w/w) |
| Silicone 245 | 1.0 |
| Panthenol 50W | 1.0 |
| Zinc Gluconate | 0.1 |
| Crocamol STS | 1.0 |
| Zinc Lactate | 0.1 |
| Carbomer (Ultrez) | 0.37 |
| SDA 40B Alcohol | 67.2 |
| Water | 22.13 |
| Neutrol TE (50% sol.) | 1.7 |
| Glycerin | 0.5 |
| Propylene Glycol | 0.5 |
| Phenoxy Ethanol | 1.0 |
| 1,2 Octanediol | 3.0 |
| Farnesol | 0.5 |

| Health Care Hand Disinfectant Formulation with emollient solvents and essential oil/and/or ingredients (General Formula 2) | |
| --- | --- |
| Constituent | % (w/w) |
| Silicone Oil | 0.5-2.0 |
| Derivative of Pantothenic Acid | 0.5-2.0 |
| Soluble Zinc Salt #1 | 0.05-0.2 |
| Alkylpropoxylate | 0-1.0 |
| Soluble Zinc Salt #2 | 0.05-0.3 |
| Essential Oil/and or constituents | 0.3-1.0 |
| Fatty Alcohol | 0-1.0 |
| Alcohol | 50-70 |
| Water | 15-30 |
| Poluquaternium 10 | 0.05-0.3 |
| Hydroxyalkylcellulose | 0.05-0.3 |
| Glycerin | 0.5-2.0 |
| Propylene Glycol | 0.5-2.0 |
| Emollient Solvent | 0.5-5.0 |
| Phenoxyethanol | 0.3-1.0 |
| Alkyarylpropoxylate | 0-2.0 |

| Health Care Hand Disinfectant Formulation with emollient solvents and essential oil/and/or ingredients (Specific Formula) | |
| --- | --- |
| Constituent | % (w/w) |
| Silicone Oil | 0.5 |
| Panthenol 50W | 1.0 |
| Zinc gluconate | 0.1 |
| Procetyl 10 | 0.5 |
| Zinc lactate | 0.1 |
| Farnesol | 0.5 |
| SDA 40 B Alcohol | 75.9 |
| Water | 16.6 |
| U care JR 30 | 0.2 |
| Methocell K4MS | 0.1 |
| Glycerin | 0.5 |
| Propylene Glycol | 1.0. |
| 1,2 Octanediol | 2.0 |
| Phenoxyethanol | 1.0 |

| ANTI-IRRITANT SKIN PROTECTANT CREAM (General Formulation) | |
| --- | --- |
| INGREDIENT | % (Grams/100 Grams) |
| Soluble Zinc Salt 1 | 0.2-4 |
| Soluble Zinc Salt 2 | 0-1.0 |
| Soluble Zinc Salt 3 | 0-1.0 |
| Acetylated Lanolin Alcohol | 1-3 |
| Allantoin | 0.5-1 |
| Biguanide | 0.05-0.5 |
| Hydroxylated Milk Glyceride | 0.5-2.0 |
| Alkyalkylate | 0.5-2.5 |
| Germall Plus (ISP Sutton) [Diazolidinyl Urea & Iodopropynyl Buylcarbamate] | 0.1-0.3 |
| Fatty Quaternary Amine Salt | 0.1-2.0 |
| Fatty Alcohol | 0.3-6.0 |
| Chitosan | 0.2-1.0 |
| Emulsifying Wax | 0.5-5 |
| Polyethylene oxide | 0.05-2 |
| Water | 50-75 |
| Silicone Oil | 0.2-1 |
| Polyquaternium 10 | 0.1-0.3 |
| Vitamin E | 0.3-1 |
| Insoluble Zinc Salt | 0.4-10 |
| Alcohol | 0-50 |

Biguanide: Chlorhexidine or PHMB

| ANTI-IRRITANT SKIN PROTECTANT CREAM (Specific Formulation) | |
| --- | --- |
| INGREDIENT | % (Grams/100 Grams) |
| Gel: | |
| Zinc Gluconate | 3.00 |
| Purified Water | 6.00 |
| Cream Base: | |
| Acetulan | 2.60 |
| Allantoin | 0.56 |
| Chlorhexidine Gluconate, 20% | 0.25 |
| Cremerol HMG | 1.20 |
| Crodamol MM | 2.20 |
| Germall Plus | 0.25 |
| Incroquat Behenyl TMS | 3.00 |
| Kytamer PC | 0.25 |
| Polawax NF | 5.00 |
| Polyox WSR 205 | 0.10 |
| Purified Water | 70.69 |
| Silicone (polydimethylsiloxane), 350 cs | 0.30 |
| Ucare JR-400 | 0.20 |

ANTI-IRRITANT SKIN PROTECTANT CREAM (Specific Formulation)

| INGREDIENT | % (Grams/100 Grams) |
| --- | --- |
| Vitamin E Oil | 0.40 |
| Zinc Stearate | 4.00 |

ANTIMICROBIAL HAND CREAM (General Formulation)

| INGREDIENT | % (Grams/100 Grams) |
| --- | --- |
| Biguanide | 0.2-4.0 |
| Polyquaternium 10 | 0.1-0.4 |
| Water | 25-40 |
| Soluble Zinc Salt #1 | 1-5 |
| Insoluble Zinc Salt | 0.5-4 |
| Soluble Zinc Salt #2 | 0-1 |
| Soluble Zinc Salt #3 | 0-1 |
| Acetylated Lanolin Alcohol | 0.5-1 |
| Lanolin Alcohol | 0.4-1 |
| Hydroxylated Milk Glyceride | 0.2-1 |
| Germall Plus (ISP Sutton) [Diazolidinyl Urea & Iodopropynyl Buylcarbamate] | 0.05-0.3 |
| Alkyl Glucosides | 0.5-1 |
| Fatty Quaternary Amine Salt | 0.1-2 |
| Fatty Alcohol | 0.3-6.0 |
| Ester of Fatty Acid and Alkyl Alcohol | 0.5-2 |
| Chitosan | 0.05-0.5 |
| Emulsifying Wax | 0.5-5 |
| Polyethylene oxide | 0.02-0.5 |
| Chlorophenol Antimicrobial | 0.1-0.3 |
| Vitamin E | 0.05-0.5 |
| Water | 18-30 |
| SDA Alcohol | 0-50 |
| Silicone Oil | 0.5-1 |
| Allantoin | 0.1-0.2 |

Biguanide: Chlorhexidine or PHMB

ANTIMICROBIAL HAND CREAM

| INGREDIENT | % (Grams/100 Grams) |
| --- | --- |
| Chlorhexidine Gluconate | 3.500 |
| Ucare JR-400 | 0.350 |
| Water | 32.025 |
| Zinc Gluconate | 4.375 |
| Zinc Stearate | 3.500 |
| Acetulan | 0.533 |
| Amerchol L-101 | 0.444 |
| Cremerol HMG | 0.222 |
| Germaben II | 0.289 |
| Glucam E-20 | 0.888 |
| Incroquat Behenyl TMS | 1.332 |
| Isopropyl Myristate | 1.155 |
| Kytamer PC | 0.089 |
| Polawax | 2.220 |
| Polyox WSR-205 | 0.033 |
| Triclosan | 0.135 |
| Vitamin E-Acetate | 0.089 |
| Water | 25.721 |
| Chlorhexidine Gluconate | 0.500 |
| Alcohol (100% ethanol) | 20.000 |
| Silicone (polydimethylsiloxane), 350 cs | 0.500 |
| Allantoin | 0.100 |
| Water | 2.000 |
| Total | 100.000 |

Glove/condom coating Anti irritant Emulsion (General Formula). These formulations contain an anti irritant composition consisting of two or more soluble Zinc salts and one or more insoluble zinc salts, Panthenol and a film forming hydrogel.

| INGREDIENT | % (Grams/100 Grams) |
| --- | --- |
| Soluble Zinc Salt #1 | 0.1-1 |
| Soluble Zinc Salt #2 | 0.1-1 |
| Polyquaternium 10 | 0.05-0.5 |
| Derivative of Pantothenic Acid | 0.5-5 |
| Soluble Zinc Salt #3 | 0.1-1 |
| Insoluble Zinc Salt #1 | 0.1-1 |
| Insoluble Zinc Salt #2 | 0-0.5 |
| Alkyl Polyol | 0.5-10 |
| Water | 5-20 |
| Silicone Emulsion | 70-95 |

Glove Coating Anti irritant Emulsion (Specific formula)

| INGREDIENT | % (Grams/100 Grams) |
| --- | --- |
| Zinc Acetate | 0.40 |
| Zinc Gluconate | 0.30 |
| Ucare JR-30M | 0.05 |
| D,L-Panthenol, 50W | 1.00 |
| Zinc Lactate | 1.60 |
| Zinc Oxide | 0.20 |
| Glycerin | 3.00 |
| Purified Water | 10.00 |
| Silicone Emulsion | 83.45 |

Glove Coating Anti irritant Antimicrobial Emulsion (General Formula I)

| INGREDIENT | % (Grams/100 Grams) |
| --- | --- |
| Soluble Zinc Salt #1 | 0.1-1 |
| Soluble Zinc Salt #2 | 0.1-1 |
| Polyquaternium 10 | 0.05-0.5 |
| Derivative of Pantothenic Acid | 0.5-5 |
| Soluble Zinc Salt #3 | 0.1-1 |
| Insoluble Zinc Salt #1 | 0.1-1 |
| Insoluble Zinc Salt #2 | 0-0.5 |
| Alkyl Polyol | 0.5-10 |
| Water | 5-20 |
| Silicone Emulsion | 70-95 |
| Biguanide | 0.3-4.0 |
| Chlorinated phenol | 0-1.0 |
| Quaternary ammonium compound | 0-0.2 |
| Emollient solvent | 0-3 |

Anti irritant/antimicrobial glove/condom coating formulation (General Formula 2)

| Components | % (w/w) |
| --- | --- |
| Zinc gluconate | 0.2-0.5 |
| Zinc lactate | 0.8-1.6 |
| Zinc acetate | 0.1-0.4 |
| D,L Panthenol 50W | 1.0-3.0 |
| U care JR 30 (Polyquaternium 10) | 0.05-0.1 |
| Zinc oxide | 0.2-0.5 |
| Glycerin | 2.0-5.0 |
| Silicone fluid | 0-3.0 |
| Propylene Glycol | 0-2.0 |
| Water | 3.0-25 |

-continued

Anti irritant/antimicrobial glove/condom coating formulation (General Formula 2)

| Components | % (w/w) |
|---|---|
| Chlorhexidine gluconate | 0-4.0 |
| Phenoxyethanol | 0-1.0 |
| Triclosan | 0-0.5 |
| Silicone/cationic Polyurethane Slurry | 70-90 |

Glove Coating anti irritant antimicrobial Emulsion (specific formula A)

| INGREDIENT | % (Grams/100 Grams) |
|---|---|
| Zinc Acetate | 0.40 |
| Zinc Gluconate | 0.30 |
| Ucare JR-30M | 0.05 |
| D,L-Panthenol, 50W | 1.00 |
| Zinc Lactate | 1.60 |
| Zinc Oxide | 0.20 |
| Glycerin | 3.00 |
| Purified Water | 10.00 |
| Silicone Emulsion | 83.45 |
| Chlorhexidine gluconate | 2.00 |

Glove Coating anti irritant antimicrobial Emulsion (specific formula B)

| INGREDIENT | % (Grams/100 Grams) |
|---|---|
| Zinc Acetate | 0.40 |
| Zinc Gluconate | 0.30 |
| Ucare JR-30M | 0.05 |
| D,L-Panthenol, 50W | 1.00 |
| Zinc Lactate | 1.60 |
| Zinc Oxide | 0.20 |
| Glycerin | 3.00 |
| Purified Water | 10.00 |
| Silicone Emulsion | 81.05 |
| Chlorhexidine gluconate | 2.00 |
| Triclosan | 0.05 |

Method of preparation of anti irritant/antimicrobial slurry for coating of Gloves/Condoms
Method 1
Anti irritant/Chlorhexidine Slurry

| Constituents | % (w/w) |
|---|---|
| Phase A | |
| Water | 4.8 |
| Chlorhexidine gluconate (20% solution) | 20 |
| Zinc acetate | 0.2 |
| Zinc Lactate | 1.0 |
| D,L Panthenol 50 W | 1.0 |
| U-Care JR 30 | 0.05 |
| Zinc gluconate | 0.3 |
| Mix until all ingredients are dissolved | |
| Phase B | |
| Glycerin | 2.25 |
| Zinc oxide | 0.4 |
| Make a uniform suspension | |

Add phase A to phase B and mix. Add 70 gm Silicone or Cationic Polyurethane slurry and mix well.

This slurry is applied on the inner/inner+outer surface of the glove/condom.

Method 2
Anti irritant/Chlorhexidine Slurry

| Constituents | % (w/w) |
|---|---|
| Phase A | |
| Water | 4.8 |
| Chlorhexidine gluconate (20% solution) | 20 |
| Zinc acetate | 0.2 |
| Zinc Lactate | 1.0 |
| D,L Panthenol 50W | 1.0 |
| U-Care JR 30 | 0.05 |
| Zinc gluconate | 0.3 |
| Mix until all ingredients are dissolved | |
| Add | |
| Zinc oxide | 0.4 |
| Make a uniform suspension | |

Add phase A to 70 gm Silicone or Cationic Polyurethane slurry and mix well.

This slurry is applied on the inner or inner+outer surface of the glove/condom.

Method 3
Anti irritant/Chlorhexidine/Triclosan Slurry

| Constituents | % (w/w) |
|---|---|
| Phase A | |
| Water | 4.5 |
| Chlorhexidine gluconate (20% solution) | 15.0 |
| Zinc acetate | 0.2 |
| Zinc Lactate | 1.0 |
| D,L Panthenol 50W | 1.0 |
| U-Care JR 30 | 0.05 |
| Zinc gluconate | 0.3 |
| Mix until all ingredients are dissolved | |
| Phase B | |
| Triclosan | 0.3 |
| Phenoxy ethanol | 0.5 |
| Propylene Glycol | 1.5 |
| Glycerin | 0.75 |
| Zinc oxide | 0.4 |
| Make a uniform suspension | |

Add phase A to 74.5 gm Silicone or Cationic Polyurethane slurry and mix well. This slurry is applied on the inner/inner+outer surface of the glove/condom.

Method 4
Anti irritant/Chlorhexidine/Triclosan Slurry

| Constituents | % (w/w) |
|---|---|
| Phase A | |
| Water | 4.5 |
| Chlorhexidine gluconate (20% solution) | 15.0 |
| Zinc acetate | 0.2 |
| Zinc Lactate | 1.0 |

| -continued | |
|---|---|
| D,L Panthenol 50W | 1.0 |
| U-Care JR 30 | 0.05 |
| Zinc gluconate | 0.3 |
| Mix until all ingredients are dissolved | |
| Add Zinc oxide | 0.4 |
| Phase B | |
| Triclosan | 0.3 |
| Phenoxy ethanol | 0.5 |
| Propylene Glycol | 1.5 |
| Make a uniform suspension | |

Add phase A to phase B and mix. Add 74.75 gm Silicone or Cationic poly urethane slurry and mix well.

This slurry is applied on the inner/inner+outer surface of the glove/condom.

| Diaper Rash Cream # D | |
|---|---|
| Constituent | % (w/w) |
| Water | 55.5 |
| Zinc gluconate | 0.5 |
| Zinc lactate | 0.5 |
| Zinc acetate | 0.2 |
| Germal+ | 0.2 |
| Panthenol 50W | 1.0 |
| Allantoin | 0.2 |
| Ucare Jr 30 | 0.2 |
| Petroleum jelly | 15 |
| Incoquat | 2.0 |
| Polowax | 2.0 |
| Stearyl alcohol | 2.0 |
| Sorbitan oleate | 1.0 |
| Isopropyl Myristate | 1.0 |
| Plyoxyl 40 stearate | 1.0 |
| Glycerin | 2.0 |
| Tocopherol acetate | 0.5 |
| Silicone fluid | 10 |
| Zinc oxide | 3.0 |
| Zinc stearate | 2.0 |

| Hand disinfectant N.A | |
|---|---|
| Constituent | % (w/w) |
| Farnesol | 0.5 |
| Procetyl-10 (Croda) | 0.5 |
| U Care JR 30M (Amerchol) | 0.2 |
| Panthenol 50W (BASF) | 1.0 |
| Propylene glycol | 1.0 |
| Zinc gluconate | 0.1 |
| Glucam P.20 | 0.5 |
| Zinc lactate | 0.1 |
| 1,2-octanediol | 3.0 |
| Methocell K4MS (Dow) | 0.1 |
| Phenoxyethanol | 0.5 |
| Alcohol (SDA-3C) | 70.0 |
| Water | 22.5 |

Anti irritant Zinc gel composition for use in various topical products. The present invention provides for an anti irritant zinc gel composition comprising one or more organic zinc salt at a concentration between 0.05-2.0% w/w, D,L panthenol at a concentration between 0.5-5.0% w/w and a gelling agent such as cationic hydroxyl ethyl cellulose (Polyquaternium 10) at a concentration of 0.05-0.3% w/w, hydroxyl alkyl cellulose at a concentration between 0-0.3% w/w, polyethylene oxide at a concentration of 0-0.3% w/w, cellulose acetate polymers such as cellulose acetate phthalate at a concentration of 0-0.3% w/w, and water at a concentration of 1-10% w/w. Suitable zinc salts for use in these formulations include zinc acetate (molar solubility in water of 1.64 moles/l), zinc butyrate (molar solubility in water of 0.4 moles/l), zinc citrate (molar solubility in water of <0.1 moles/l), zinc gluconate (molar solubility in water of 0.28 moles/l), zinc glycerate (moderately water soluble), zinc glycolate (moderately water soluble), zinc formate (molar solubility in water of 0.33 moles/l), zinc lactate (molar solubility in water of 0.17 moles/l), zinc picolinate (moderately water soluble), zinc propionate (molar solubility in water of 1.51 moles/l), zinc salicylate (low water solubility), zinc tartrate (moderately water soluble) and zinc undecylenate (moderately water soluble). This zinc gel can further contain one or more zinc salts which exhibit little or no water solubility such as zinc oxide and/or zinc stearate at a concentration of 0.2-3% w/w. The zinc gel may further comprise glycerin (0-5% w/w), polyglycerol (0-5% w/w) and silicone (0-8% w/w). The zinc gel ingredients at the above concentrations are mixed and incorporated into various products (the concentrations given are the final concentration in the product when the zinc gel is mixed). Suitable products include but not limited to acne treatment products, alcohol-based waterless personal care hand sanitizers, after shave lotions, antibacterial soaps, antifungal creams and ointments, cortisone creams, deodorants, depilatories, daiper rash creams for both infants and adults, facial make-up products, first-aid creams, hand and body creams, gels and lotions, hand and body soaps, hand and body wipes and towelettes, oral care gels, mouth washes and rinses, shaving creams and gels, sunscreen formulations and sun blocks, surface wipes, vaginal applications, such as creames, gels and washes, products such as bandages, gloves and other natural latex or synthetic rubber products. The zinc gels can be prepared using the following general formula for use in various products.

| Zinc Gel General Formula | |
|---|---|
| Components | % (w/w) |
| Zinc gluconate | 0.05-2.0 |
| Zinc lactate | 0-2.0 |
| Zinc acetate | 0-2.0 |
| D,L Panthenol 50W | 0.5-5.0 |
| Polyquaternium 10 | 0.05-0.3 |
| Hydroxyalkyl cellulose | 0-0.3 |
| Polyethylene oxide | 0-0.3 |
| Cellulose acetate phthalate | 0-0.3 |
| Zinc oxide | 0-5.0 |
| Zinc stearate | 0-5.0 |
| Glycerin | 0-5.0 |
| Silicone fluid | 0-8.0 |
| Polyglycerol | 0-5.0 |
| Water | 1-10 |

Zinc gel ingredients can be added directly to a product at the desired concentration or stock solution containing 10-20 times the concentration required in the products (10x-20x) can be prepared and 5-10% of the stock Zinc gel can be used in the products to render them anti irritant. See below.

Example-1

| Zinc Gel General Formula (10X) | |
| --- | --- |
| Components | % (w/w) |
| Zinc gluconate | 0.5-20 |
| Zinc lactate | 0-20 |
| Zinc acetate | 0-20 |
| D,L Panthenol 50W | 5-50 |
| Polyquaternium 10 | 0.5-3.0 |
| Hydroxyalkyl cellulose | 0-3.0 |
| Polyethylene oxide | 0-3.0 |
| Cellulose acetate phthalate | 0-3.0 |
| Zinc oxide | 0-50 |
| Zinc stearate | 0-50 |
| Glycerin | 0-50 |
| Silicone fluid | 0-80 |
| Polyglycerol | 0-50 |
| Water | 1-10 |

10% of the zinc gel can be incorporated in the product. The zinc gel composition can vary depending on the product in which it is used.

Example-2

| Zinc gel A-1 (% in the product) (for use in Glove/Condom coating solution) | |
| --- | --- |
| Components | % (w/w) |
| Zinc gluconate | 0.3 |
| Zinc lactate | 1.6 |
| Zinc acetate | 0.2 |
| D,L Panthenol 50W | 1.0 |
| U care JR 30 (Poly quaternium 10) | 0.05 |
| Zinc oxide | 0.2 |
| Glycerin | 3.0 |
| Water | 5.0 |

Example-3

| Zinc gel A-2 (% in the product) (for use in Glove coating antimicrobial solution), General Formula | |
| --- | --- |
| Components | % (w/w) |
| Zinc gluconate | 0.3-1.0 |
| Zinc lactate | 0.5-1.0 |
| Zinc acetate | 0.1-0.3 |
| D,L Panthenol 50W | 1-1.5 |
| U care JR 30 (Poly quaternium 10) | 0.02-0.05 |
| Zinc oxide | 0.2-0.5 |
| Glycerin | 3.0 |
| Water | 5.0 |

| Zinc gel A-2 (% in the product)(for use in Glove coating antimicrobial solution), Specific Formula | |
| --- | --- |
| Components | % (w/w) |
| Zinc gluconate | 0.3 |
| Zinc lactate | 1.0 |
| Zinc acetate | 0.2 |
| D,L Panthenol 50W | 1.0 |
| U care JR 30(Poly quaternium 10) | 0.05 |
| Zinc oxide | 0.4 |
| Glycerin | 3.0 |
| Water | 5.0 |

Example 4

| Zinc gel B (for use in topical antimicrobial creams) | |
| --- | --- |
| Components | % (w/w) |
| Zinc gluconate | 0.3 |
| D,L Panthenol 50W | 1.0 |
| U care JR 30(Polyquaternium 10) | 0.05 |
| Zinc oxide | 0.2 |
| Zinc stearate | 0.2 |
| Glycerin | 3.0 |
| Water | 5.0 |

Example-5

| Zinc gel C(for use in wound healing creams) | |
| --- | --- |
| Components | % (w/w) |
| Zinc gluconate | 0.2 |
| Zinc lactate | 0.2 |
| Zinc acetate | 0.1 |
| D,L Panthenol 50W | 1.0 |
| U care JR 30(Poly quaternium 10) | 0.05 |
| Zinc oxide | 0.1 |
| Glycerin | 3.0 |
| Water | 5.0 |

Example 6

| Zinc gel D-1 (for use in alcohol based hand disinfectants) | |
| --- | --- |
| Components | % (w/w) |
| Zinc gluconate | 0.2 |
| Zinc lactate | 0.2 |
| D,L Panthenol 50W | 1.0 |
| U care JR 30(Polyquaternium 10) | 0.05 |
| Hydroxy propyl methyl cellulose | 0.1 |
| Water | 5.0 |

Zinc gel D-2: (for use in alcohol based hand disinfectants)

| Components | % (w/w) |
|---|---|
| Zinc gluconate | 0.1 |
| Zinc lactate | 0.1 |
| D,L Panthenol 50W | 1.0 |
| U care JR 30(Poly quaternium 10) | 0.05 |
| Hydroxy propyl methyl cellulose | 0.1 |
| Water | 5.0 |

Zinc gel D-3 (for use in alcohol based hand disinfectants)

| Components | % (w/w) |
|---|---|
| Zinc gluconate | 0.2 |
| D,L Panthenol 50W | 1.0 |
| U care JR 30(Poly quaternium 10) | 0.05 |
| Hydroxy propyl methyl cellulose | 0.1 |
| Water | 5.0 |

Zinc gel E (use in non-antimicrobial disinfectant soaps)

| Components | % (w/w) |
|---|---|
| Zinc gluconate | 0.1 |
| Zinc lactate | 0.05 |
| D,L Panthenol 50W | 1.0 |
| U care JR 30(Poly quaternium 10) | 0.05 |
| Water | 5.0 |

Zinc gel F: (for use in antimicrobial disinfectant soaps)

| Components | % (w/w) |
|---|---|
| Zinc gluconate | 0.1 |
| D,L Panthenol 50W | 1.0 |
| U care JR 30(Polyquaternium 10) | 0.05 |
| Water | 5.0 |

Zinc gel G: (for use in Band Aids and wound dressings)

| Components | % (w/w) |
|---|---|
| Zinc gluconate | 0.4 |
| D,L Panthenol 50W | 2.0 |
| U care JR 30(Poly quaternium 10) | 0.1 |
| Zinc oxide | 0.4 |
| Water | 5.0 |

(0.05-0.2 gm zinc gel/1 $cm^2$ was applied on the dressing or Band Aid)

Zinc gel H: (for use in topical anti irritant creams)

| Components | % (w/w) |
|---|---|
| Zinc gluconate | 0.3 |
| Zinc lactate | 0.3 |
| Zinc acetate | 0.2 |
| D,L Panthenol 50W | 1.0 |
| U care JR 30(Polyquaternium 10) | 0.05 |
| Zinc oxide | 0.2 |
| Zinc stearate | 0.2 |
| Glycerin | 3.0 |
| Diglycerol | 3.0 |
| Water | 5.0 |

Zinc gel I (for use in Adult Diaper rash creams)

| Components | % (w/w) |
|---|---|
| Zinc gluconate | 0.5 |
| Zinc lactate | 0.4 |
| Zinc acetate | 0.1 |
| D,L Panthenol 50W | 1.0 |
| U care JR 30(Polyquaternium 10) | 0.1 |
| Zinc oxide | 3.0 |
| Zinc stearate | 1.0 |
| Glycerin | 3.0 |
| Diglycerol | 3.0 |
| Water | 5.0 |

Zinc gel J (for use in Baby Diaper rash creams)

| Components | % (w/w) |
|---|---|
| Zinc gluconate | 0.2 |
| Zinc lactate | 0.2 |
| Zinc acetate | 0.1 |
| D,L Panthenol 50W | 1.0 |
| U care JR 30(Polyquaternium 10) | 0.1 |
| Zinc oxide | 3.0 |
| Zinc stearate | 1.0 |
| Glycerin | 3.0 |
| Diglycerol | 3.0 |
| Water | 5.0 |

Products in which a zinc gel formulation of the invention can be incorporated to render them anti irritant include:

Acne treatment products
Alcohol-based waterless personal care hand sanitizers
After shave lotions and gels
Antibacterial soaps
Antifungal creams and ointments
Antiseptic household first-aid creams and ointments
Cortisone creams
Deodorants
Depilatories
Diaper rash creams for both infants and adults
Facial make-up products
First aid creams
Hand and body creams, gels and lotions
Hand and body soaps
Hand and body wipes and towelettes
Oral care gels, mouth washes and rinses
Shaving creams and gels
Sunscreen formulations and sun blocks Surface wipes
Vaginal applications, such as creams, gels and washes
products such as bandages, gloves and other natural latex or synthetic rubber products

Diaper Rash Cream (General formula)

| Constituent | % (w/w) |
|---|---|
| Water | 40-60 |
| Zinc gluconate | 0.2-0.5 |
| Zinc lactate | 0.2-0.5 |
| Zinc acetate | 0.1-0.5 |
| Germal+ | 0-0.3 |
| Panthenol 50W | 1.0-5.0 |
| Allantoin | 0-0.5 |
| Ucare JR 30 | 0.1-0.5 |
| Petrolatum | 10-40 |
| Incroquat Behenyl TMS | 0-2.0 |
| Polowax N.F | 0-2.0 |
| Stearyl alcohol | 0-2.0 |
| Sorbitan oleate | 0-1.0 |
| Isopropyl Myristate | 0-1.0 |
| Plyoxyl 40 stearate | 0-1.0 |
| Glycerin | 1-5.0 |
| Diglycerol | 1-5.0 |
| Vitamin E | 0.2-0.5 |
| Silicone fluid | 2-8.0 |
| Zinc oxide | 1-5.0 |
| Zinc stearate | 1-5.0 |
| Mineral oil | 0-5.0 |

Psoraisis treatment cream (General Formula)

| Constituent | % (w/w) |
|---|---|
| Water | 40-60 |
| Zinc gluconate | 0.2-0.5 |
| Zinc lactate | 0.2-0.5 |
| Zinc acetate | 0.1-0.5 |
| Zins salicylate | 0-0.5 |
| Germal+ | 0-0.3 |
| Panthenol 50W | 1.0-5.0 |
| Allantoin | 0-0.5 |
| Ucare JR 30 | 0.05-0.5 |
| Petrolatum | 10-40 |
| Incroquat Behenyl TMS | 0-2.0 |
| Polowax N.F | 0.2-2.0 |
| Stearyl alcohol | 0-2.0 |
| Sorbitan oleate | 0-1.0 |
| Isopropyl Myristate | 0-1.0 |
| Polyoxyl 40 stearate | 0-1.0 |
| Glycerin | 1.0-5.0 |
| Vitamin E | 0.2-0.5 |
| Silicone fluid | 0-1.0 |
| Zinc oxide | 1.0-5.0 |
| Zinc stearate | 1.0-5.0 |
| Salicylic acid | 1.0-3.0 |
| Chamomile Extract | 0-0.2 |
| Water | 50-70 |

Anti irritant/antimicrobial formulation for application to wound dressing, Band-Aid, Wipes etc.

| Components | % (w/w) |
|---|---|
| Zinc gluconate | 0.2-0.4 |
| D,L Panthenol 50W | 1.0-2.0 |
| U care JR 30(Polyquaternium 10) | 0.05-3.0 |
| Zinc oxide | 0.1-0.5 |
| Water | 60-80 |
| Essential oil ingredient | 0-0.5 |
| Emollient solvent | 0-3.0 |
| Quaternary ammonium compound | 0-0.3 |
| Biguanide | 0-0.3 |
| Glycerine | 5.0-15 |
| Diglycerol | 5.0-15 |

(0.05-0.2 gm zinc gel formulation/1 $cm^2$ was applied on the dressing or Band Aid)

Topical anti irritant creams/lotion

| Components | % (w/w) |
|---|---|
| Zinc gluconate | 0.2-0.3 |
| Zinc lactate | 0.1-0.3 |
| Zinc acetate | 0-0.2 |
| D,L Panthenol 50W | 1.0-5.0 |
| U care JR 30(Polyquaternium 10) | 0.05-0.1 |
| Zinc oxide | 0.1-1.0 |
| Glycerin | 1.0-3.0 |
| Mineral oil | 0-8.0 |
| Propylene glycol | 0-2.0 |
| Petrolatum | 2.0-5.0 |
| Stearyl alcohol | 1.0-3.0 |
| Crodalan AWS | 1.0-2.0 |
| Incroqurt Behenyl TMS | 1.0-2.0 |
| Polawax | 1.0-2.0 |
| Germal+ | 0.15-0.3 |
| Vitamin E | 0.1-0.5 |
| Water | 50-90 |

Topical anti irritant anti microbial cream

| Components | % (w/w) |
|---|---|
| Zinc gluconate | 0.2-0.3 |
| Zinc lactate | 0.1-0.3 |
| Zinc acetate | 0-0.2 |
| D,L Panthenol 50W | 1.0-5.0 |
| U care JR 30(Polyquaternium 10) | 0.05-0.1 |
| Zinc oxide | 0.1-1.0 |
| Glycerin | 1.0-3.0 |
| Mineral oil | 0-8.0 |
| Propylene glycol | 0-2.0 |
| Petrolatum | 2.0-5.0 |
| Stearyl alcohol | 1.0-3.0 |
| Crodalan AWS | 1.0-2.0 |
| Incroquat Behenyl TMS | 1.0-2.0 |
| Polawax | 1.0-2.0 |
| Germal+ | 0.15-0.3 |
| Vitamin E | 0-1-0.5 |
| Water | 50-90 |
| Essential oil/Essential oil ingredient | 0.3-0.5 |
| Emollient solvent | 0-2.0 |
| Quaternary ammonium compound | 0-0.3 |
| Biguanide | 0-0.3 |
| Polymixin | 0-0.3 |
| Neosporin | 0-0.3 |
| Bacitracin | 0.0.5 |
| Miconazole | 0.2-2.0 |

Burn Wound/decubitus Ulcer Treatment Creams

| Components | % (w/w) |
|---|---|
| Water | 50-80 |
| Zinc gluconate | 0.2-0.3 |
| D,L Panthenol 50W | 1.0-5.0 |
| U care JR 30(Polyquaternium 10) | 0.05-0.1 |
| Zinc oxide | 0.1-1.0 |
| Glycerin | 1.0-3.0 |
| Mineral oil | 0-8.0 |
| Propylene glycol | 0-2.0 |
| Petrolatum | 2.0-30 |
| Stearyl alcohol | 1.0-20 |
| Incroquat Behenyl TMS | 0-2.0 |
| Polawax | 0-2.0 |
| Germal+ | 0.15-0.3 |
| Vitamin E | 0-0.5 |
| Sorbitan oleate | 1.0-5.0 |
| Isopropyl Myristate | 1.0-5.0 |
| Polyoxyl 40 stearate | 1.0-5.0 |
| Silver sulfadiazine | 1.0-2.0 |
| Chlorhexidine gluconate | 0-0.05 |
| Phenoxy ethanol | 0-1.0 |
| Essential oil | 0-1.0 |
| Essential oil ingredient | 0-1.0 |
| Emollient solvent | 0-2.0 |

The table below shows some of the general class of compounds and specific compounds used in the formulations in this application. In the formulas provided herein, where a specific compound is listed, another specific compound within the same general class may be substituted.

| General class of compounds | Specific compounds |
|---|---|
| Essential Oil/and or constituents | All essential oils, Sesqiterpenoids such as farnesol |
| Emollient solvents | Sensiva, Hexanediol, Octanediol, Symdiol |
| Alkylpropoxylate | Procetyl.10, |
| Polyquaternium 10 | U care |
| Derivative of Pantothenic Acid | Panthenol |
| Alkyl Glycol | Glucam P.20, E.20 |
| Soluble Zinc Salt #1 | |
| Alkylarylpropoxylate | Crodamol STS |
| Soluble Zinc Salt #2 | |
| Quaternary Ammonium Compounds | BZK, BZT |
| Hydroxyalkylcellulose | Hydroxypropyl metyl cellulose |
| Quaternary conditioners | Incroquat B65C, Incroquat behenyl TMS Incroquat B-65 C |
| Biguanide | Chlorhexidine, PHMB |
| Alcohol | Ethanol, Isopropanol (SDA-40.B, SDA-3C) |
| Quaternised foaming coconut oils | Montaline C-40 |
| Organic acids | Citric acid, sorbic acid, Lactic acid etc. |

Example

An Anti Irritant Antimicrobial Composition for use in Topical Creams, Skin Disinfectants and Medical Devices such as Glove, Condom and Wound Dressings Anti irritant antimicrobial compositions (AIR-AM Compositions) comprising (A) antimicrobials; and/or (B) Antimicrobials+essential oil ingredients and/or (C) emollient solvents+essential oil ingredients and/or (D) a combination of (A)+(C) were developed for use in topical creams, skin disinfectants, and for fabricating and/or coating medical articles such as glove, condom and wound dressings to render them anti irritant and infection resistant. The AIR-AM compositions contained a mixture of zinc salts in specific proportions (two or more Soluble zinc salts (0.2-2.0%) such as Zinc gluconate, Zinc lactate and/or Zinc acetate, and insoluble zinc salt such as zinc oxide and Zinc stearate (0.2-2.0%)), a hydrogel. (poly quaternium 10,hydroxyl alkyl cellulose), panthenol, and optionally a silicone fluid. The AIR-AM compositions further contained one or more antimicrobial agent, such as (1) one or more cationic/nonionic antimicrobial agent (e.g., Biguanides, Silver salts chlorinated phenols, Quaternary ammonium compounds etc.) and/or (2) a synergistic combination of antimicrobial and essential oil ingredients, and/or (3) a synergistic combination of certain emollient solvents+essential oil ingredients and/or (4) a combination of (1) and (3). These compositions may be used either alone or in a polymeric matrix such as silicone, polyurethane, polylactic acid etc to coat natural and synthetic glove, condom wound dressings etc, or may be incorporated into topical creams or skin disinfectants. It was observed that coating latex glove material with such anti-irritant compositions inactivated proteins and chemicals believed to be associated with skin irritation Evaluation of the inactivation of allergenic latex proteins and other chemicals by the coated in the glove.

A topical cream containing 4% zinc gluconate gel significantly reduced skin irritation in volunteers who exhibited Type IV hypersensitivity when exposed to latex gloves. This cream also prevented dermal irritation induced by sodium lauryl sulfate (Dermatitis March 2005 vol. 16, page 22). However in 10-20% of the individuals tested, this cream containing 3% zinc gluconate gel itself exhibited a stinging effect when applied on the skin, even without a latex glove (Dermatitis March 2005 vol. 16, page 22). We prepared topical creams containing lower concentration of Zinc gluconate gel (0.3-0.5%) which did not cause the stinging effect. However this cream was not as effective as the 3% cream in reducing latex related contact dermatitis. We investigated the anti irritant efficacy of lower concentration of Zinc gluconate (0.1-0.5%) in combination with other soluble zinc salts. e.g. Zinc lactate (0.2-1.0%). Zinc acetate (0.2-0.4%) and insoluble Zinc salts e.g. Zinc oxide (0-2.0%) and Zinc stearate (0-4%).

We have developed a Zinc Gel containing Zinc gluconate 0.3-0.5%, Zinc lactate 0.8-1.8%, Zinc acetate 0.2-0.4% and Zinc oxide 0.2-0.8% Hydrogel 0.05-0.1% (Polyquaternium 10) and Panthenol 0.5-1.0%. This was incorporated in a silicone polymer slurry and used for coating latex gloves.

Effectiveness Testing

Reduction in Soluble Latex Protein: This testing focused on the soluble latex proteins extractable from a latex glove. Not all of the soluble protein produces antigenic responses; therefore the measured reduction level of the antigenic proteins may be even greater than that for the total soluble extract. These proteins have been denoted as latex proteins, using a generic nomenclature to describe the wide variety of proteinaceous materials normally present in natural latex rubber.

Method:

The Zinc Gel formulation was added into the silicone slurry used to coat latex gloves. The silicone slurry was prepared fresh for this testing. The gloves were coated both on the inside and outside with the silicone slurry containing the Zinc Gel. The outside coating was washed off and the gloves were dried.

Three sets of gloves were prepared:
1) Control Glove: Coating with silicone slurry (Ansell);
2) Two sets of Test Gloves: Coated with silicone slurry containing two different concentrations of Zinc Gel. Both additive levels can be used to manufacture gloves. The purpose was to determine if increasing the level would also increase effectiveness.

Method of determination of Latex proteins in glove fingers: The glove fingers were cut and suspended in water (1 gm/8 ml) and extracted for 2 hours at 70° C. The extract was collected after centrifugation. The latex protein in the extract was precipitated by adding ammonium sulfate to the extract to a concentration of 45% and left for 24 hours. The precipitate was collected after centrifugation and dissolved in water. This protein extraction was read at 280 nm in a UV/VIS Spectrophotometer.

Results:

|  | Peak Value for Å |  |
| --- | --- | --- |
| Control glove* | 0.48 | 0.411 |
| Test glove - 1.2% Concentration | 0.12 | — |
| Test glove - 1.7% Concentration | — | 0.039 |
| % Protein Reduction | 75% | 90.5% |

*Tests were run at different times, therefore two sets of Control Gloves were used.
NOTE:
The Zinc Gel used was not intended to be an optimum formulation. The purpose here was to determine the feasibility of to reduce the irritants present in natural rubber latex. The levels used were chosen because they are consistent with that used in other skin care preparations. The applicability of incorporating into the glove coating emulsion has been shown.

Conclusion: As noted in the above table, the soluble latex proteins were reduced 90% by using a 1.7% level. This level was readily incorporated into the silicone dipping emulsion without compromising either the donning ability or the powder-free status of the gloves. The 1.7% level may be sufficient to inactivate all soluble proteins that may be released in use. The soluble latex proteins were extracted at 70° C., whereas in common use the protein extraction will take place at under 37° C.

Direct Reduction of Total Extracted Materials The application for determination in the reduction of total extractable materials is described below. Since the previous section focused on the effect of on the soluble latex proteins extracted from a glove, a test was performed to determine the effectiveness against the extractable total materials—catalysts, fillers, stabilizers, cross-linking agents. Many people who are not allergic to the proteins do react to these other materials. It is of key interest to determine the effectiveness of in reducing total glove extractables—whether or not they cause irritation.

A UV/VIS Spectrophotometer was used to determine the reduction in total materials extractable from latex gloves. Extracts from Ansell gloves using immersion in distilled water at 60° C. with agitation gave a consistent and strong peak at 268 nm wavelength The percent reduction in the materials extracted was determined by adding a stock solution of Zinc gel to the glove extract, vortexing for three minutes, centrifuging the mixture for 15 minutes at 3300 RPM and measuring the optical density at 268 nm wavelength. The glove extract without the Zinc Gel was also processed the same way and measured the initial O.D The percent reduction in O.D of treated extract from that of the untreated extract was calculated. The results of this testing are shown below.

| Total %* | % Reduction in Total Extractables | % Reduction in Soluble Latex Proteins |
| --- | --- | --- |
| 0.190 | 33.0 | |
| 0.682 | 33.3 | |
| 1.210 | 34.5 | 75.0 |
| 1.700 | 36.1 | 90.5 |
| 2.300 | 39.1 | |
| 4.470 | 42.5 | |
| 7.704 | 45.5 | |
| 13.740 | 57.3 | |
| 18.320 | 66.7 | |

*This is a nominal value representing the percent of Zinc necessary to add to the silicone dipping emulsion to elicit the noted effect.

| Preparation of Anti irritant antimicrobial coating composition for gloves and condoms. | |
| --- | --- |
| Ingredients | % (w/w) |
| Arlasilk phospholipid CDM | 0-1.0 |
| D, L or D, Panthenol | 0.25-1.0 |
| Propylene glycol | 0.-0.75 |
| Zinc acetate | 0.2-0.4 |
| Zinc lactate | 0.5-1.8 |
| Zinc gluconate | 0.2-0.5 |
| Phenoxyethanol | 0.5-0.75 |
| Zinc oxide | 0.2-1.0 |
| Sensiva | 0.-2.0 |
| Farnesol | 0.-1.0 |
| Water | 20-25 |
| Benzathonium chloride or Benzalkonium chloride | 0-0.3 |
| Chlorinated phenol | 0-0.5 |
| U care JR 30 | 0.05-0.1 |
| Silicone slurry | 65-75 |
| Silicon fluid | 0-1.0 |
| Chlorhexidine gluconate | 3-4 |

Glove coating procedure: 100 ml of the Coating slurry is taken in a tray and is placed in the tray and the tray is kept on a rotary shaker and rotated for 1 slurry gets inside the glove during the process. The glove is removed from the at 700° C. for 40 minutes. The outer surface of the glove is rinsed in water and is dried again at 70° C. for 1 hour.

Preparation of coated gloves:

Chlorhexidin glove (CHG glove)

Chlorhexidine+Famesol glove (CHG++F glove)

Chlorhexidine+Farnesol+BZT glove (CHG++F+BZT glove)

Chlorhexidine+Famesol+Triclosan glove (CHG++F+T glove)

Chlorhexidine+ES+F glove (CHG+ES+F glove)

These gloves were prepared using the following specific formulations:

| | % (w/w) | | | | |
| --- | --- | --- | --- | --- | --- |
| Ingredients | CHG | CHG + F | CHG + F + BZT | CHG + F + ES | CHG + F + T |
| Triclosan | 0 | 0 | 0 | 0 | 0.3 |
| D, L Panthenol | 1.0 | 1.0 | 1.0 | 1.0 | 1.0 |
| Zinc acetate | 0.3 | 0.3 | 0.3 | 0.3 | 0.3 |
| Zinc lactate | 1.0 | 1.0 | 1.0 | 1.0 | 1.0 |
| Benzathonium chloride | 0 | 0 | 0.2 | 0 | 0 |

-continued

| Ingredients | % (w/w) | | | | |
|---|---|---|---|---|---|
| | CHG | CHG + F | CHG + F + BZT | CHG + F + ES | CHG + F + T |
| U care JR 30 | 0.1 | 0.1 | 0.1 | 0.1 | 0.1 |
| Zinc gluconate | 0.3 | 0.3 | 0.3 | 0.3 | 0.3 |
| Water | 15.45 | 14.45 | 14.95 | 13.95 | 13.65 |
| Farnesol | 0 | 1.0 | 1.0 | 1.0 | 1.0 |
| Zinc oxide | 0.8 | 0.8 | 0.8 | 0.8 | 0.8 |
| Sensiva | 0 | 0 | 0 | 0.5 | 0 |
| Phospholipid CDM | 0 | 0 | 0 | 0 | 0.5 |
| Silicone slurry | 60 | 60 | 60 | 60 | 60 |
| Silicon D C 3225C | 0.3 | 0.3 | 0.3 | 0.3 | 0.3 |
| Phenoxyethanol | 0.75 | 0.75 | 0.75 | 0.75 | 0.75 |
| Chlorhexidine gluconate (20%) | 20 | 20 | 20 | 20 | 20 |

Anti Irritant Anti Microbial Composition for Coating Wound Dressings

Anti irritant for use in wound dressings contains Zinc gluconate 0.3-0.5%, Zinc lacate 0.5-1.0% quaternium 10 (U Care JR 30) 0.1-0.2% Panthenol 0.5-1.0% zinc oxide 0.1-0.5%. The following antimicrobial composition containing the (Zinc gluconate 0.5%, Zinc lactate 1.0%, U Care JR 30 0.1% Panthenol 50 W 1.0% Zinc oxide 0.2%) were prepared and used to coat the wound dressing. J&J Band-Aid was used as the dressing.

1) 0.3% Famesol+1.0% Sensiva+0.5% Phospholipid (PL)

2) 0.3% Farnesol+1.0% Sensiva+0.5% PL+1.0% Colloidal Ag 3) 0.3% Famesol+1.0% Sensiva+0.5% PL+0.2% Ag carbonate (Ag C)

4) 0.3% Famesol+1.0% Sensiva+0.5% PL+0.2% AgC+0.3% PHMB 5) 0.15% PHMB+0.1% BZK+0.1% Triclosan Zinc Gel alone was also used to coat the dressing and tested along with uncoated dressing

| Zone of inhibition (mm) against S. aureus ATCC# 10390 | | |
|---|---|---|
| Group | Zone size (around the dressing) | Subculture from under the bandage |
| 1 | 3.0 × 5.0 | 0 |
| 2 | 2.5 × 4.0 | 0 |
| 3 | 3.5 × 4.5 | 0 |
| 4 | 5.0 × 8.0 | 0 |
| 5 | 15 × 10 | 0 |
| Zinc Gel | 1.0 × 2.0 | 40 |
| Uncoated Dressing (Control) | 0 | $>10^2$ |

| Zone of inhibition (mm) against E. coli | | |
|---|---|---|
| | Zone size | Subculture from under the bandage |
| 1 | 0 × 0.5 | $3.0 \times 10^2$ |
| 2 | 0.5 × 0.3 | $2.0 \times 10^2$ |
| 3 | 1.0 × 1.0 | 0 |
| 4 | 0 × 4.5 | 0 |
| 5 | 10 × 8 | 0 |
| Zinc Gel | 0 × 0.5 | 29 |
| Control | 0 | $>10^2$ |

An Anti Irritant Antimicrobial Alcohol Based Hand Disinfectant

The anti irritant in this disinfectant contains zinc gluconate 0.1-0.3%; Zinc lactate 0.1-0.3%; panthenol 0.5-1.0%; polyquaternium 10 0.1-0.3%; and silicone fluid 0.-0.5% The antimicrobial composition in this disinfectant contains only emollient solvents (Ethylhexylglycerin, Octanediol, phospholipids complexes etc.) 1-3.0%, essential oil ingredients (Sesquiterpenoids such as Famesol) 0.5-2.0%.

| Anti irritant antimicrobial Surgical Hand disinfectant A | |
|---|---|
| Constituent | % (w/w) |
| Farnesol | 1.5. |
| Glucam P 20 | 0.5 |
| U Care JR 30M (Amerchol) | 0.20 |
| Panthenol 50W (BASF) | 1.0 |
| Zinc gluconate | 0.10 |
| Zinc lactate | 0.20 |
| Octoxy glycerine | 2.0 |
| Phospholid CDM | 2.0 |
| Propylene glycol | 1.0 |
| Alcohol (SDA-40B) | 72.6 |
| Water | 18.9 |

In Vitro Pig Skin Model for Evaluation of Immediate and Persistent Efficacy of Surgical Hand Disinfectants Against Resident Flora This in vitro method was developed to simulate the FDA-TFM glove juice method in evaluating the immediate and persistent efficacy of alcohol-based surgical hand rubs after a single application of the formulation. The skin of freshly killed pig from a slaughter house was obtained, treated, cut into small pieces, disinfected with alcohol and dried.

Method of Testing Immediate Efficacy (a) Inoculation and incubation: Each of the two skin pieces was contaminated with 50 μl of S. epidermidis($10^8$ cfu/ml) and the two pieces were rubbed against each other for 15 sec. The skin-pairs were then kept in a plastic tray, (skin-side facing upwards). The skin-pairs were then covered with a cotton-gauze and sufficient quantity of saline (0.9%) (about 2-3 ml per skin-piece) was spread on the skin to avoid drying of the skin. The tray was covered with aluminum foil and then incubated at 37° C. for 2 hours. (The skin-pairs inoculated with the culture after incubation mimics a human hand with the resident flora).

(b) Hand disinfectant application: At the end of the incubation period, the cotton-gauze pieces were removed from the skin-pairs and discarded. 30 μl of the surgical hand rub was applied on each piece of the pig skin and the two skins were rubbed against each-other for 30 sec. (This step mimics the application of the surgical hand rub onto the human hand).

(c) Recovery of microorganisms: Phosphate Buffered Saline (PBS) (0.2 ml) was then put on one of the skin pair and the two skins were rubbed together for 15 sec. The surviving microorganisms from the skin were recovered by rinsing the two skins with 4.9 ml of the PBS for each skin by using a pipette and the washings were collected together in a small Petri dish. (This step mimics the sampling of the human hand with the PBS by the glove juice method.) The contents of the Petri dish were then transferred to a culture tube, vortexed and 1.0 ml of this washing was then immediately transferred to a tube containing 9.0 ml of Drug Neutralizing Broth, suitably serially diluted and an aliquot was plated on TSA to determine microbial count. For control, the skin was treated in a similar way except that PBS was used instead of test formulations.

The colony counts of bacteria for each skin-pair were converted to its $log_{10}$ values and their means were determined. In order to compare the efficacies of the test formulation, the term reduction factor (RF) was coined and defined as follows:

Reduction factor(RF)=$M_{PBS}-M_{Test}$

Comparison of the reduction in bacterial counts (RF) of Disinfectant A and Avagard in the in vitro pig skin model

| | Pig Skin Model | |
|---|---|---|
| Product | Mean* counts ($log_{10}$) in pig skin (SD) | RF |
| Disinfectant A | 3.99 (0.424) | 3.04 |
| Avagard ™ | 4.11 (0.354) | 2.92 |
| Control (PBS) | 7.03 (0.057) | — |

RF: Reduction factor in the pig skin model

Conclusion: The anti irritant antimicrobial disinfectant containing the and the antimicrobial composition containing essential oil ingredient and emollient solvents is equally effective as a disinfectant containing an antimicrobial agent (CHG 1.0%)

Evaluation of Antimicrobial Efficacy

Methods

Challenge Suspensions of S aureus and E. Coli: Immediately prior to initiating the test procedure, an initial suspension of each challenge species containing approximately $1\times10^8$ CFU/ml was prepared as follows: The broth cultures (18-24 hours old) were diluted with Trypticase soy Broth (TSB) media to 0.3 O.D/ml measured at 600 nm in spectrophotometer. These cultures are estimated to have contained approximately $1\times10^8$ cfu organism/ml as determined previously by serial dilution and subculture. These cultures were used to prepare the challenge suspensions in TSB. Final challenge suspensions containing approximately $1\times10^7$ CFU/ml of each bacterial strain were prepared by diluting the $10^8$ CFU/ml suspension in TSB and vortexing thoroughly.

Testing Procedure:

Glove Material Preparation and Inoculation: Prior to initiating the test procedure, the middle 3 fingers of each of the 3 coated and each of the 3 control gloves were aseptically cut and 5.0 cm length measured from the closed tip were marked in each glove.

Preparation of Inoculum: 1.0 ml of $10^7$ cfu organism/ml prepared as described earlier were mixed with 5.0 ml Bovine serum+4.0 ml TSB ($1\times10^6$ cfu/ml inoculum). Fingers of each glove were inoculated with 0.1 ml of the above inoculum ($10^5$CFU of organism) of a challenge species.

The inoculum was spread within the 5 cm marked area for 20 seconds by lightly massaging the area. After 1 minute, 0.9 ml neutralizing media was added, and the area again massaged for 1 minute. Fluid was then collected from the glove finger and transferred into 49 ml of Drug Neutralizing Broth (DNB) in 125 ml sterile Polypropylene tube and vortex for approximately 1 minute. Ten-fold dilutions (e.g., $10^{-1}$, $10^{-2}$, and $10^{-3}$) were then prepared in DNB. 0.5 ml aliquots from the appropriate dilutions were pour-plated, in duplicate, using Trypticase Soy Agar with product neutralizer. These plates were incubated at 35°±2° C. for forty-eight (48) to seventy-two (72) hours, or until sufficient growth was observed. Following incubation, the colonies on the plates were counted manually using a hand-tally counter.

Results:

| Bacterial counts in Glove Finger (cfu/finger) | | |
|---|---|---|
| Group | S aureus | E. coli |
| Control (uncoated) | $1.7 \times 10^5$ | $1.1 \times 10^5$ |
| 1) CHG glove | $2.0 \times 10^3$ | $1.0 \times 10^2$ |
| 2) CHG + F glove | $3.1 \times 10^2$ | 96 |
| 3) CHG + ES + F glove | $1.0 \times 10^2$ | 53 |
| 4) CHG + F + BZT | 0 | 0 |
| 5) CHG + F + T | 90 | 90 |

Conclusion: Significant reduction in bacterial counts was seen in all the anti irritant antimicrobial gloves. The group containing CHG+F+BZT appears to be superior in efficacy.

Various publications and have been referenced herein, the contents of which are hereby incorporated by reference in their entireties.

We claim:

1. A coating for application to an article, comprising:
   two water soluble zinc salts, each at a concentration of between 0.1 and 1 weight percent;
   a first water insoluble zinc salt at a concentration of between about 0.1 and 1 weight percent;
   panthenol at a concentration of between about 0.05 and 5 weight percent; and
   glycerin, at a concentration between about 0 and 5 weight percent.

2. The coating according to claim 1, further comprising a third water soluble zinc salt at a concentration of between 0.1 and 1 weight percent.

3. The coating according to claim 1 or 2, wherein the combined amounts of all water soluble zinc salts is between about 0.1 and 0.5 weight percent.

4. The coating according to claim 1 or 2, where the water soluble zinc salts are selected from the group consisting of zinc acetate, zinc butyrate, zinc gluconate, zinc glycerate, zinc glycolate, zinc formate, zinc lactate, zinc picolinate, zinc priopionate, zinc salicylate, zinc tartrate, and zinc undecylenate.

5. The coating according to claim 3, where the water soluble zinc salts are selected from the group consisting of zinc acetate, zinc butyrate, zinc glycerate, zinc gluconate, zinc glycolate, zinc formate, zinc lactate, zinc picolinate, zinc priopionate, zinc salicylate, zinc tartrate and zinc undecylenate.

6. The coating according to claim 1, 2, 3 or 4, further comprising a second water insoluble zinc salt.

7. The coating according to claim 6, wherein the first or second water insoluble zinc salt is selected from the group consisting of zinc oxide, zinc stearate, zinc phosphate, zinc carbonate, zinc borate and zinc citrate.

8. A coating for application to an article, comprising:
two water soluble zinc salts, each at a concentration of between 0.1 and 1 weight percent;
panthenol at a concentration of between about 0.05 and 5 weight percent; and
an effective amount of an antimicrobial agent.

9. The coating of claim 8, where the antimicrobial agent is selected from the group consisting of biguanides, iodophors, quaternary ammonium compounds, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylenol, foscarnet, miconazole, fluconzaole, itriconazole and ketoconazole.

10. The coating according to claim 8, further comprising a third water soluble zinc salt at a concentration of between 0.1 and 1 weight percent.

11. The coating according to claim 8, 9, or 10, wherein the combined amounts of all water soluble zinc salts is between about 0.1 and 0.5 weight percent.

12. The coating according to claim 8, 9 or 10 where the water soluble zinc salts are selected from the group consisting of zinc acetate, zinc butyrate, zinc glycerate, zinc gluconate, zinc glycolate, zinc formate, zinc lactate, zinc picolinate, zinc priopionate, zinc salicylate, zinc tartrate and zinc undecylenate.

13. The coating according to claim 11, where the water soluble zinc salts are selected from the group consisting of zinc acetate, zinc butyrate, zinc glycerate, zinc gluconate, zinc glycolate, zinc formate, zinc lactate, zinc picolinate, zinc priopionate, zinc salicylate, zinc tartrate and zinc undecylenate.

14. The coating according to claim 8, further comprising a water insoluble zinc salt.

15. The coating according to claim 14, wherein the water insoluble zinc salt is selected from the group consisting of zinc oxide, zinc citrate, zinc phosphate, zinc carbonate, zinc borate and zinc stearate.

16. The coating of claim 1 or 2, further comprising an emollient solvent at a concentration of less than 5 weight percent.

17. The coating of claim 6, further comprising an emollient solvent at a concentration of less than 5 weight percent.

18. The coating of claim 7, further comprising an emollient solvent at a concentration of less than 5 weight percent.

19. The coating of claim 8, further comprising an emollient solvent at a concentration of less than 5 weight percent.

20. The coating of claim 9, further comprising an emollient solvent at a concentration of less than 5 weight percent.

21. The coating of claim 10, further comprising an emollient solvent at a concentration of less than 5 weight percent.

22. The coating of claim 11, further comprising an emollient solvent at a concentration of less than 5 weight percent.

23. The coating of claim 12, further comprising an emollient solvent at a concentration of less than 5 weight percent.

24. The coating of claim 13, further comprising an emollient solvent at a concentration of less than 5 weight percent.

25. The coating of claim 14, further comprising an emollient solvent at a concentration of less than 5 weight percent.

26. The coating of claim 15, further comprising an emollient solvent at a concentration of less than 5 weight percent.

27. An article having a surface to which a coating according to claim 1 has been applied.

28. An article having a surface to which a coating according to claim 2 has been applied.

29. An article having a surface to which a coating according to claim 3 has been applied.

30. An article having a surface to which a coating according to claim 4 has been applied.

31. An article having a surface to which a coating according to claim 5 has been applied.

32. An article having a surface to which a coating according to claim 6 has been applied.

33. An article having a surface to which a coating according to claim 7 has been applied.

34. An article having a surface to which a coating according to claim 8 has been applied.

35. An article having a surface to which a coating according to claim 9 has been applied.

36. An article having a surface to which a coating according to claim 10 has been applied.

37. An article having a surface to which a coating according to claim 11 has been applied.

38. An article having a surface to which a coating according to claim 12 has been applied.

39. An article having a surface to which a coating according to claim 13 has been applied.

40. An article having a surface to which a coating according to claim 14 has been applied.

41. An article having a surface to which a coating according to claim 15 has been applied.

42. An article having a surface to which a coating according to claim 16 has been applied.

43. An article having a surface to which a coating according to claim 17 has been applied.

44. An article having a surface to which a coating according to claim 18 has been applied.

45. An article having a surface to which a coating according to claim 19 has been applied.

46. An article having a surface to which a coating according to claim 20 has been applied.

47. An article having a surface to which a coating according to claim 21 has been applied.

48. An article having a surface to which a coating according to claim 22 has been applied.

49. An article having a surface to which a coating according to claim 23 has been applied.

50. An article having a surface to which a coating according to claim 24 has been applied.

51. An article having a surface to which a coating according to claim 25 has been applied.

52. An article having a surface to which a coating according to claim 26 has been applied.

53. A surgical hand wash, comprising:
(i) two or more water soluble zinc salts wherein said zinc salts in total are present at a combined concentration of between about 0.1 and 0.5 percent (weight/weight);
(ii) farnesol at a concentration of between about 0.3 and 1.0 percent (weight/weight);
(iii) panthenol at a concentration of between about 0.2 and 5 percent (weight/weight); and
(iv) a quaternary ammonium compound and a biguanide, wherein the total concentration of quaternary ammonium compound and biguainde is between about 0.05 and 2.0 percent (weight/weight).

54. The surgical hand wash of claim 53, wherein the zinc salts are zinc gluconate, present at a concentration of between about 0.10-0.25 percent (weight/weight) and zinc lactate, present at a concentration of about between about 0.10-0.25 percent (weight/weight).

55. A disinfectant soap, comprising:
(i) two or more water soluble zinc salts, wherein said zinc salts in total are present at a combined concentration of between about 0.1 and 0.5 percent (weight/weight);
(ii) farnesol at a concentration of between about 0.3 and 1.0 percent (weight/weight);
(iii) panthenol at a concentration of between about 0.2 and 5 percent (weight/weight); and
(iv) a quaternary ammonium compound and a second antimicrobial agent selected from the group consisting of a biguanide and a chlorinated phenol, wherein the total concentration of quaternary ammonium compound and second antimicrobial agent is between about 0.05 and 2.0 percent (weight/weight).

56. The disinfectant soap of claim 55, wherein the zinc salts are zinc gluconate, present at a concentration of between about 0.10-0.25 percent (weight/weight) and zinc lactate, present at a concentration of about between about 0.10-0.25 percent (weight/weight).

57. The disinfectant soap of claim 55, further comprising phenoxyethanol at a concentration of between about 0.3 and 1 percent (weight/weight).

58. The disinfectant soap of claim 56, further comprising phenoxyethanol at a concentration of between about 0.3 and 1 percent (weight/weight).

59. A composition comprising:
at least one water soluble zinc salt at a concentration of between about 0.05 and 2.0% w/w;
D,L panthenol at a concentration between about 0.05 and 5.0% w/w; and
a gelling agent at a concentration of between about 0.05 and 0.3% w/w; where the composition provides an anti-irritant effect.

60. The composition of claim 59, further comprising hydroxylalkyl cellulose at a concentration of less than about 0.3% w/w.

61. The composition of claim 59, further comprising polyethylene oxide at a concentration of less than about 0.3% w/w.

62. The composition of claim 60, further comprising polyethylene oxide at a concentration of less than about 0.3% w/w.

63. The composition of claim 59, further comprising a cellulose acetate polymer at a concentration of less than about 0.3% w/w.

64. The composition of claim 60, further comprising a cellulose acetate polymer at a concentration of less than about 0.3% w/w.

65. The composition of claim 61, further comprising a cellulose acetate polymer at a concentration of less than about 0.3% w/w.

66. The composition of claim 62, further comprising a cellulose acetate polymer at a concentration of less than about 0.3% w/w.

67. An article having a surface to which a coating according to claim 59 has been applied.

* * * * *